United States Patent
McAlister

(10) Patent No.: US 9,193,925 B2
(45) Date of Patent: Nov. 24, 2015

(54) RECYCLING AND REINVESTMENT OF CARBON FROM AGRICULTURAL PROCESSES FOR RENEWABLE FUEL AND MATERIALS USING THERMOCHEMICAL REGENERATION

(75) Inventor: Roy Edward McAlister, Phoenix, AZ (US)

(73) Assignee: McAlister Technologies, LLC, Phoenix, AZ (US)

( * ) Notice: Subject to any disclaimer, the term of this patent is extended or adjusted under 35 U.S.C. 154(b) by 0 days.

(21) Appl. No.: 13/584,554

(22) Filed: Aug. 13, 2012

(65) Prior Publication Data

US 2013/0205647 A1   Aug. 15, 2013

Related U.S. Application Data

(60) Provisional application No. 61/523,247, filed on Aug. 12, 2011.

(51) Int. Cl.
*C10L 1/02* (2006.01)
*C07C 1/04* (2006.01)
*C07C 29/151* (2006.01)

(52) U.S. Cl.
CPC ............... *C10L 1/02* (2013.01); *C07C 1/0405* (2013.01); *C07C 29/1518* (2013.01); *C10L 1/023* (2013.01); *Y02E 50/18* (2013.01)

(58) Field of Classification Search
CPC ......... C10L 1/02; C10L 1/0405; C10L 1/023; C07C 29/1518; Y02E 50/18
USPC .................................. 44/300; 568/700, 840
See application file for complete search history.

(56) References Cited

U.S. PATENT DOCUMENTS

| | | | |
|---|---|---|---|
| 2,180,626 | A | 11/1939 | Delorme |
| 4,339,546 | A | 7/1982 | Randalls |
| 4,787,321 | A | 11/1988 | Schnellbacher et al. |
| 5,343,699 | A | 9/1994 | McAlister |
| 5,882,484 | A | 3/1999 | Pyy |
| 6,024,032 | A | 2/2000 | Sharpe |
| 6,133,328 | A | 10/2000 | Lightner |
| 6,155,212 | A | 12/2000 | McAlister |
| 6,270,731 | B1 | 8/2001 | Kato et al. |
| 6,446,597 | B1 | 9/2002 | McAlister |
| 6,890,419 | B2 | 5/2005 | Reichman et al. |
| 7,033,570 | B2 | 4/2006 | Weimer et al. |
| 7,033,822 | B2 | 4/2006 | Maston |
| 7,132,090 | B2 | 11/2006 | Dziedzie et al. |
| 7,138,046 | B2 | 11/2006 | Roychowdhury |
| 7,169,821 | B2 | 1/2007 | Branson |
| 7,309,435 | B2 | 12/2007 | Rozich |
| 7,375,142 | B2 * | 5/2008 | Pearson ............... 518/706 |
| 7,425,315 | B2 | 9/2008 | Kruesi |
| 7,482,078 | B2 | 1/2009 | Sridhar et al. |
| 7,491,453 | B2 | 2/2009 | Logan et al. |
| 7,507,341 | B2 | 3/2009 | Gallagher et al. |
| 7,562,708 | B2 | 7/2009 | Cogliandro et al. |
| 7,569,203 | B2 | 8/2009 | Fridman et al. |
| 7,572,369 | B2 | 8/2009 | Gallagher et al. |
| 7,572,530 | B2 | 8/2009 | Gottmann et al. |
| 7,575,822 | B2 | 8/2009 | Mitlitsky et al. |
| 7,591,880 | B2 | 9/2009 | Levan et al. |
| 7,599,760 | B2 | 10/2009 | Dutta et al. |
| 7,608,439 | B2 | 10/2009 | Offerman et al. |
| 7,618,606 | B2 | 11/2009 | Fan et al. |
| 7,628,137 | B1 | 12/2009 | McAlister |
| 7,753,973 | B2 | 7/2010 | Galloway |
| 7,878,131 | B2 | 2/2011 | Becchetti et al. |
| 7,906,559 | B2 | 3/2011 | Olah et al. |
| 7,931,783 | B2 | 4/2011 | Dam-Johansen et al. |
| 7,931,997 | B2 | 4/2011 | Gottmann et al. |
| 7,947,155 | B1 | 5/2011 | Green et al. |
| 8,012,453 | B2 | 9/2011 | Saxena |
| 8,022,260 | B2 | 9/2011 | O'Connor et al. |
| 8,070,835 | B2 | 12/2011 | McAlister |
| 8,071,246 | B2 | 12/2011 | Mitlitsky et al. |
| 8,211,583 | B2 | 7/2012 | Weingaertner et al. |
| 8,226,798 | B2 | 7/2012 | van Aardt et al. |
| 8,318,997 | B2 | 11/2012 | McAlister |
| 2002/0077401 | A1 | 6/2002 | Chaudhary et al. |

(Continued)

FOREIGN PATENT DOCUMENTS

| | | |
|---|---|---|
| JP | 2005-289856 | 10/2005 |
| JP | 2007-314745 | 12/2007 |

(Continued)

OTHER PUBLICATIONS

Bill, Alain, Carbon Dioxide Hydrogenation to Methanol at Low Pressure and Temperature, Ecole Polytechnique Federale De Lausanne, 1998, Thesis No. 1726. pp. 1-3 ,9,10,23,48.*
"Geologic Sequestration of Carbon Dioxide | UIC | US EPA." US Environmental Protection Agency. Accessed: Aug. 30, 2009. <http://www.epa.gov/safewater/uic/wells_sequestration.html>. pp. 1-5.
"NETL: What Is Carbon Sequestration?" US Department of Energy—National Energy Technology Laboratory. Accessed: Aug. 30, 2009. <http://www.netl.doe.gov/technologies/carbon_swq/FAQs/carbon-seq.html>.
"US EPA—Carbon Sequestration in Agriculture and Forestry: Frequently Asked Questions." US Environmental Protection Agency. Published: Oct. 19, 2006. Accessed: Aug. 30, 2009. <http://www.epa.gov/sequestration/faq.html>.
Colls, Alison. "Carbon Sequestration." Environmental Change Institute. Accessed: Aug. 30, 2009. <http://climatex.org/articles/climate-change-info/carbon-sequestration/>. pp. 1-4.
Richard, Michael Graham. "Important! Why Carbon Sequestration Won't Save Us." TreeHugger. Published: Jul. 31, 2006.<http://treehugger.com/files/2006/07/carbon_sequestration.php>. pp. 1-6.
Salleh, Anna. "Urea 'Climate Solution' May Backfire." ABC.net.au. Published: Nov. 9, 2007. Accessed: Aug. 30, 2009. <http://www.abc.net.au/science/articles/2007/11/09/2085584.htm>. pp. 1-3.

(Continued)

*Primary Examiner* — Cephia D Toomer
(74) *Attorney, Agent, or Firm* — Perkins Coie LLP

(57) ABSTRACT

Techniques, systems, apparatus and material are disclosed for regeneration or recycling of carbon substances into renewable fuel and materials. In one aspect, a method of recycling carbon to produce a renewable fuel can include harvesting carbon donors, such as carbon dioxide ($CO_2$), emitted from an agricultural process. Hydrogen donors, such as from biomass waste, can be dissociated under an anaerobic reaction to produce hydrogen. The harvested carbon dioxide can be reacted with the waste-produced hydrogen under pressure and temperature to generate a renewable fuel, such as methanol fuel.

14 Claims, 12 Drawing Sheets

(56) References Cited

U.S. PATENT DOCUMENTS

| | | |
|---|---|---|
| 2004/0253168 A1 | 12/2004 | Chu |
| 2006/0280669 A1 | 12/2006 | Jones |
| 2007/0056842 A1 | 3/2007 | Roychowdhury |
| 2008/0128259 A1 | 6/2008 | Kostek et al. |
| 2008/0233029 A1 | 9/2008 | Fan et al. |
| 2009/0007484 A1 | 1/2009 | Smith |
| 2009/0183430 A1 | 7/2009 | Schubert et al. |
| 2009/0208784 A1 | 8/2009 | Perry et al. |
| 2009/0208785 A1 | 8/2009 | McElroy |
| 2009/0246596 A1 | 10/2009 | Sridhar et al. |
| 2009/0273240 A1 | 11/2009 | Gurunathan et al. |
| 2009/0291346 A1 | 11/2009 | Hickey et al. |
| 2009/0293348 A1* | 12/2009 | Olah et al. .............. 44/448 |
| 2010/0275823 A1 | 11/2010 | Pahls |
| 2010/0298450 A1 | 11/2010 | Datta et al. |
| 2011/0036320 A1 | 2/2011 | Peret |
| 2011/0070510 A1 | 3/2011 | McAlister |

FOREIGN PATENT DOCUMENTS

| | | |
|---|---|---|
| JP | 2010-031187 | 2/2010 |
| WO | WO-2005021474 A1 | 3/2005 |
| WO | WO-2007122498 A2 | 11/2007 |
| WO | WO-2009-002191 | 12/2008 |
| WO | WO-2011031752 A2 | 3/2011 |
| WO | WO-2011100695 | 8/2011 |

OTHER PUBLICATIONS

International Search Report and Written Opinion for PCT Application No. PCT/US2011/024800; Applicant: McAlister Technologies, LLC; Date of Mailing: Oct. 20, 2011; 12 pages.

International Search Report and Written Opinion for PCT Application No. PCT/US2012/050619; Applicant McAlister Technologies, LLC; Date of Mailing: Feb. 13, 2013; 16 pages.

European Search Report for Application 11742987.8; Report Dated Feb. 19, 2014; 6 pages.

\* cited by examiner

US 9,193,925 B2

RECYCLING AND REINVESTMENT OF CARBON FROM AGRICULTURAL PROCESSES FOR RENEWABLE FUEL AND MATERIALS USING THERMOCHEMICAL REGENERATION

CROSS-REFERENCE TO RELATED APPLICATION(S)

The present application claims priority to and the benefit of U.S. Provisional Patent Application No. 61/523,247, filed Aug. 12, 2011, and entitled "RECYCLING AND REINVESTMENT OF CARBON FROM AGRICULTURAL PROCESSES FOR RENEWABLE FUEL AND MATERIALS USING THERMOCHEMICAL REGENERATION," the entirety of which is incorporated by reference herein.

BACKGROUND

This application relates to devices, techniques and materials related to thermochemical regeneration of carbon dioxide into liquid fuel.

The Industrial Revolution has produced the infrastructure, mechanized equipment, appliances, and communications systems to stimulate civilization's 7 billion people to burn more than one million years of fossil coal, oil, natural gas, and shale accumulations each year.

Global-scale participation in the Industrial Revolution has produced interrelated problems of finite resource depletion and economic inflation; loss of productivity due to diseases that are initiated or exasperated by air, water, and soil pollution; lack of confidence to adopt the work ethic required for long-term achievements; and global warming that threatens to trigger more severe climate changes by releasing methane and other greenhouse gases from previously frozen soils, melting ice packs, and anaerobic processes in sediments on ocean floors, rivers, lakes, and riparian areas.

BRIEF DESCRIPTION OF THE DRAWINGS

Like reference symbols and designations in the various drawings indicate like elements.

DETAILED DESCRIPTION

Overview

Figure 1:
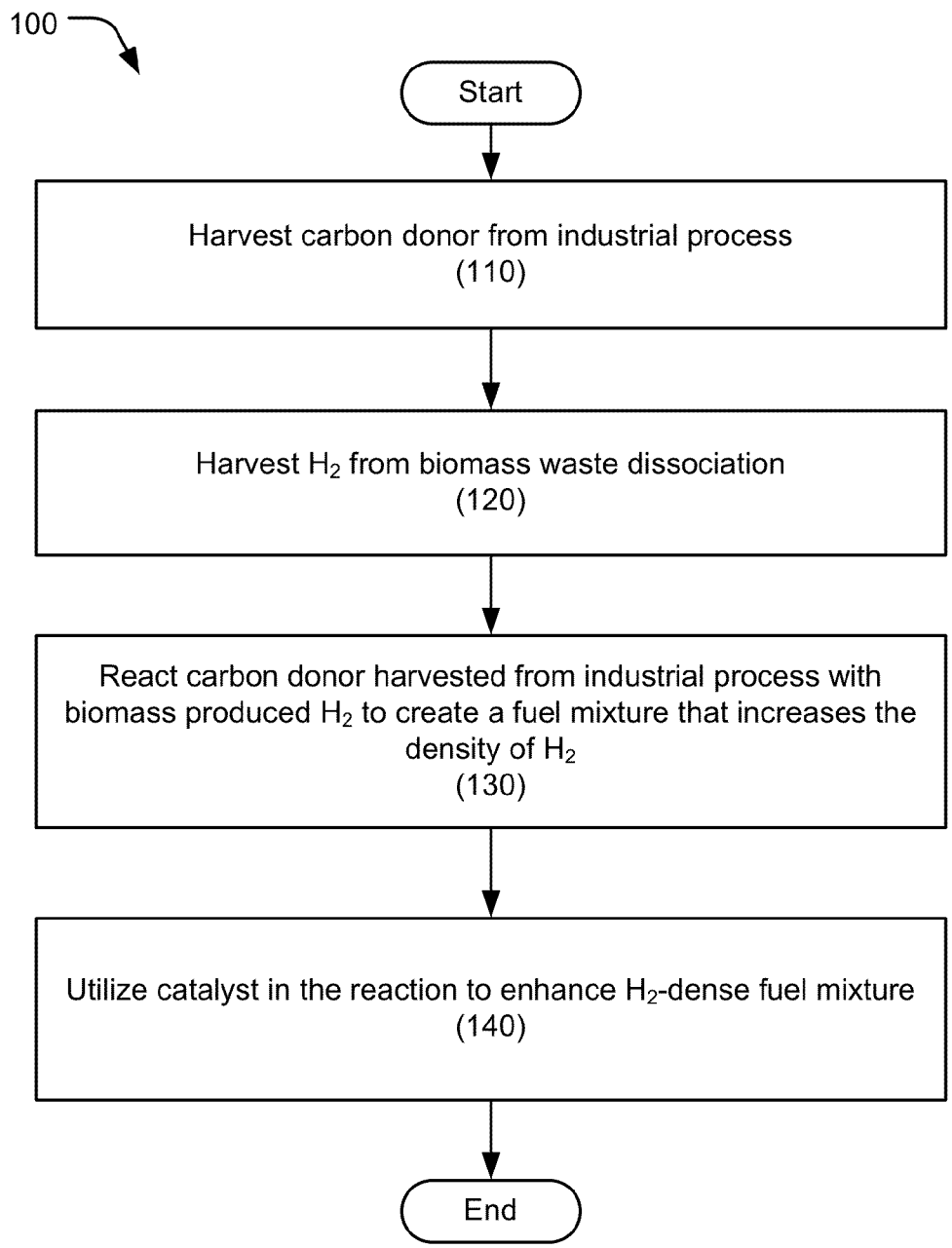
FIG. 1 is a process flow diagram of a process for reinvesting, repurposing or recycling carbon dioxide harvested from waste generated by industrial processes to react with hydrogen from biomass waste dissociation.

Techniques, systems, apparatus and materials are disclosed for thermochemical repurposing, recycling or reinvestment of carbon dioxide into liquid fuel.

In one aspect, a method of recycling carbon to produce a renewable fuel includes harvesting carbon dioxide emitted from an industrial process. Biomass waste is dissociated under an anaerobic reaction to produce hydrogen. The harvested carbon dioxide is reacted with the biomass waste produced hydrogen under pressure and heat to generate a renewable fuel.

Implementations can optionally include one or more of the following features. The renewable fuel can include at least one of alcohol, an ether, and another compound containing oxygen. The alcohol can include at least one of methanol, ethanol, propanol and butanol. The ether can include dimethyl ether (DME), diethyl ether (DEE) and various other compositions. The ethers such as DME and DEE can be converted to generate a polymer precursor to a durable good. In addition, ethylene, propylene, butylene, acetaldehyde, or cyclohexane can be used to create building block mers for dedicating carbon to durable goods production. A catalyst can be added to enhance production of the renewable fuel. The catalyst can include at least one of copper-zinc-oxide, deposited sinter mixture of copper, and copper-zinc oxide. The method can include harvesting waste heat rejected from an engine to provide heat used in the reaction. Heat or another form of energy can be generated from a renewable resource including at least one of wind, solar, moving water and geothermal energy. The method can include controlling the heat and pressure to generate a selected type of the renewable fuel. Hydrogen can be produced from dissociation of the biomass waste at a remote location and transported through a pipeline. Dissociating the biomass waste can include thermochemically producing hydrocarbons such as $CH_4$, $C_2H_6$, and or alcohols such as $CH_3OH$, $C_2H_5OH$ etc., as a transportable precursor to hydrogen and carbon production at remote locations; transporting the hydrocarbons through a pipeline; and separating the hydrocarbons into hydrogen and carbon monoxide. The method can further include cleaning the harvested carbon dioxide; and using the cleaned carbon dioxide as a nutrient for green house crops. The method can include using the cleaned carbon dioxide as a buoyant lifter in photosynthesis for plants comprising algae.

In another aspect, a method of recycling carbon to produce carbon enhanced durable goods and products along with a renewable fuel can include harvesting carbon dioxide emitted from an industrial process or harvesting nitrogen from the atmosphere. The method can include dissociating biomass waste under an anaerobic process to produce carbon monoxide, one or more carbon donors and hydrogen. Thermochemically shifted carbon monoxide and additional hydrogen can be generated by reacting the harvested carbon dioxide with the biomass waste produced by one or more carbon donors; and reacting the biomass produced carbon monoxide and the thermochemically shifted carbon monoxide with the biomass produced hydrogen and the additional hydrogen under pressure and heat to generate a renewable fuel.

Implementations can optionally include one or more of the following features. The one or more carbon donors can include at least one of hydrocarbon and alcohol. The renewable fuel can include at least one of alcohol and an ether and a nitrogenous substance. The alcohol can include at least one of methanol and ethanol. The ether can include dimethyl ether (DME) and/or diethyl ether (DEE). The method can include converting the DME to generate a polymer precursor to a durable good. Alternatively, ethylene, propylene, butylene, acetaldehyde, or cyclohexane can be used as building block mers to generate a polymer precursor to a durable good.

The method can include adding a catalyst to enhance production of the renewable fuel. The catalyst can include at least one of transition metal carbides, borides, and nitrides. The transition metal carbides, borides, and nitrides can include at least one of $Fe_3C$, $Co_3C$, $Co_3Fe_3C_2$, $Mn_3C$, $FeC_3$, $CoC_3$, $CoFeC_6$, $MnFeC_6$, $Mn_5C_2$, $MnFeC_6$, $Fe_3Cr_3C_2$, $Fe_3Co_2BNC_2$, $Fe_3VC_2$, $Fe_4NC_2$, $Fe_3MoC_2$, and $Fe_5BNC$. The method can include harvesting waste heat rejected from an engine to provide the heat used in the reaction. The method can include generating heat from a renewable energy source comprising at least one of wind and solar energy source. The method can include controlling the heat and pressure to generate a select type of the renewable fuel. Hydrogen can be produced from dissociation of the biomass waste at a remote location and transported through a pipeline. Dissociating the biomass waste can include thermochemically producing the hydrocarbon as a transportable precursor to hydrogen at a remote location, transporting the hydrocarbons through a pipeline; and separating the hydrocarbons into hydrogen and carbon monoxide. The method can further include cleaning the harvested carbon dioxide and using the cleaned carbon dioxide as a nutrient for green house crops. The method can further include using the cleaned carbon dioxide as a buoyant lifter in photosynthesis for plants comprising algae.

The described techniques and system can potentially provide one or more of the following advantages. For example, widely available hydrocarbon feedstock substances including selections such as methane from anaerobic digestion of wastes and natural gas is dissociated into carbon and hydrogen. Such carbon can be utilized to produce non-fuel products such as carbon-reinforced equipment to harness solar, wind, moving water, and geothermal energy resources. Co-produced hydrogen is thus virtually a free by-product of profitable production of carbon-enhanced products. Compared to electrolysis of water, more than four times as much hydrogen can be produced per BTU equivalent by thermal dissociation of natural gas ($CH_4$+HEAT→Carbon Products+$2H_2$).

Co-produced carbon can be used to manufacture high performance durable goods that are lighter than aluminum with greater strength and fatigue endurance than steel. Including equipment to harness solar, wind, moving water, and geothermal resources along with much lighter and stronger transportation components greatly improves fuel efficiency for delivered payloads. Application of such carbon to produce equipment that harnesses renewable resources provides many times more clean energy than burning the carbon one time and incurring environmental pollution and greenhouse gas problems.

Utilization of co-produced hydrogen in combined heat and power (CHP) engine-generators double energy utilization efficiency compared to central power plants. Also, application of fuel injector or multi-fuel injector technology in engines using hydrogen can actually clean the air that enters such engines.

Another benefit and application of such co-produced hydrogen is to react it with nitrogen from the atmosphere or carbon dioxide (from bakeries, breweries, and fossil-fired power plants, etc.) to produce liquid fuels that can be stored in tanks that now store gasoline or diesel fuel ($3H_2$+$CO_2$→$CH_3OH$+$H_2O$). This can enable widespread utilization of hydrogen extracted from methane produced from waste biomass or natural gas by conversion of existing engines at the amount of time of a tune up. The net environmental impact of utilizing nitrogenous compounds such as NH3 and/or liquid fuels such as $CH_3OH$ or another fuel alcohol to densify hydrogen for storage and/or transportation in conventional pipelines or fuel tanks is that upon use in fuel cells or heat engines is no net increase in carbon dioxide as an emission to the environment.

Thus in addition, $CO_2$, which would otherwise be released to the environment can be repurposed and recycled to generate renewable energy by reacting with hydrogen donors or carbon donors from biomass waste dissociation. Accordingly, rather than waste energy in trying to remove carbon dioxide, potentially harmful carbon can be repurposed to generate useful equipment to produce renewable energy and/or to densify and deliver hydrogen for ultimate carbon removal from the atmosphere.

Techniques, apparatus and systems are described for implementing thermochemical regeneration reactions in which carbon dioxide ($CO_2$) is harvested from industrial processes and recycled or repurposed to generate renewable fuel, such as methanol fuel. Rather than waste carbon by taking carbon out of $CO_2$, the described techniques repurpose or recycle $CO_2$ in reactions with biomass waste produced hydrogen to generate renewable fuel.

System for Recycling and Reinvestment of Carbon

FIG. 1 is a process flow diagram of a process 100 for reinvesting, repurposing or recycling carbon dioxide harvested from waste generated by industrial processes to react with hydrogen from biomass waste dissociation. A system (e.g., system 400 below) harvests a carbon donor from industrial processes (110). The carbon donor, such as carbon dioxide or carbon monoxide used in the thermochemical regeneration described here can be harvested from readily available sources of $CO_2$, such as from breweries, bakeries, central power plants, coking, calcining operations, and/or activities that burn hydrocarbons. The system obtains hydrogen from biomass waste dissociation (120). The harvested $CO_2$ can be used to produce liquid feedstocks for production of chemicals and or fuels by reacting with the biomass waste produced hydrogen (130). For example, the methanol fuel produced in the described thermochemical regeneration of $CO_2$ with $H_2$ can be used to power gasoline and diesel engines adapted to burn methanol in a non-polluting manner. U.S. Pat. No. 6,155,212 titled "METHOD AND APPARATUS FOR OPERATION OF COMBUSTION ENGINES" and U.S. Pat.

No. 6,756,140 titled "ENERGY CONVERSION SYSTEM" describe apparatus and techniques for adapting fuel cells and/or gasoline and diesel engines to burn methanol, the entire contents of which are incorporated by reference.

Reversible Equations 1 and 2 below illustrate hydrogen and carbon repurposing or recycling via an alcohol such as methanol production in which biomass produced hydrogen is reacted with industrial process produced carbon monoxide (CO) and $CO_2$ respectively.

$$CO + 2H_2 \rightarrow CH_3OH (\Delta H = -21.66 \text{ Kcal/g-mol}) \quad \text{Eqn 1}$$

$$CO_2 + 3H_2 \rightarrow CH_3OH + H_2O (\Delta H = -11.83 \text{ Kcal/g-mol}) \quad \text{Eqn 2}$$

The described thermochemical regeneration reactions that recycle or repurpose hydrogen, CO and $CO_2$ provide a bridge technology for increasing the financial return on past investments in equipment by utilizing existing fuel cells along with engine-generators, co-generation and/or transportation engines and storage tanks to enable thermochemical regeneration reactions (see Equation 5 below) to produce hydrogen-characterized fuels for achieving longer engine life and greater fuel efficiency along with greatly reduced emissions of carbon dioxide, hydrocarbons, oxides of nitrogen and particulates.

The methanol synthesis process summarized in Equations 1 and 2 may be implemented by various steps including catalytic synthesis at 95 to 100 atmospheres pressure and 500° F. (260° C.) (140). Catalysts for the processes of Equations 1 and 2 can include copper-zinc-oxide and deposited sinter mixture of copper and copper-zinc oxide at various process synthesis conditions including about 260° C. (500° F.) and 1500 psi to produce methanol or methanol and water as shown. Alternatively, dimethyl ether (DME), ethylene or propylene or diethyl ether (DEE) may be produced depending upon the pressure, temperature, catalysts, and de-hydration steps chosen.

Hydrogen used in the above described thermochemical regeneration (Equations 1-2) can be produced from biomass dissociation according to the processes summarized in Equations 3 and 4 below. The details of the biomass waste conversion are described in a U.S. patent application Ser. No. 13/027,068, now issued as U.S. Pat. No. 8,318,997, entitled "CARBON-BASED DURABLE GOODS AND RENEWABLE FUEL FROM BIOMASS DISSOCIATION," the entire contents of which are incorporated by reference. Specifically, reversible Equations 3 and 4 summarize processes for dissociating hydrocarbons, such as methane produced by biomass dissociation in an endothermic reaction to generate hydrogen and carbon.

$$C_xH_y + \text{HEAT} \rightarrow xC + 0.5_yH_2 \quad \text{Eqn 3}$$

$$CH_4 + \text{HEAT} \rightarrow C + 2H_2 (\Delta H_{298K} = 74.9 \text{ kJ/mol}) \quad \text{Eqn 4}$$

In addition to co-production by dissociation of hydrocarbon (CxHy) compounds, hydrogen can be derived by electrolytic splitting of water using any clean, alternative energy source. Also, hydrogen can be derived from a non-$CO_2$ producing anaerobic dissociation and/or co-production of hydrogen and $CO_2$ by anaerobic dissociation of organic materials and/or by utilization of energy sources such as wind, hydro, biomass, solar, tidal, geothermal, or off-peak power from coal and/or nuclear power plants. Hydrogen can also be produced from virtually any biomass waste that ordinarily rots or burns. Carbon-neutral liquid compounds for storage of hydrogen can be synthesized from hydrogen and carbon dioxide. Also, hydrogen may be produced at or near the site or delivered from pipelines that are transporting hydrogen, producer gas, or natural gas.

Methanol produced by the thermochemical regeneration reactions as described above (see Equations 1 and 2) can be inexpensive, readily storable and conveniently transportable. In one implementation of the carbon-neutral hydrogen storage operation, methanol is synthesized from sources that ordinarily source emissions of $CO_2$. Such $CO_2$ can be captured from ethanol plants, bakeries, breweries, Portland cement plants, and fossil burning power plants and/or by atmospheric "scrubbing" to extract carbon dioxide from air.

Similar to ethanol, methanol can be blended with gasoline up to 20% in conventional engines and 85% in flex fuel vehicles with no modifications to the vehicle or existing transportation fuel infrastructure. For years, methanol, with an octane rating of 100, has been used as a racing fuel for high-performance cars and dragsters.

Primary use of alcohols such as methanol as an energy carrier is economically and energetically favorable. For example, one liter of methanol at ambient temperature contains more hydrogen than one liter of liquid hydrogen that must be maintained in very cold, carefully insulated storage at −421° F.

Figure 2:
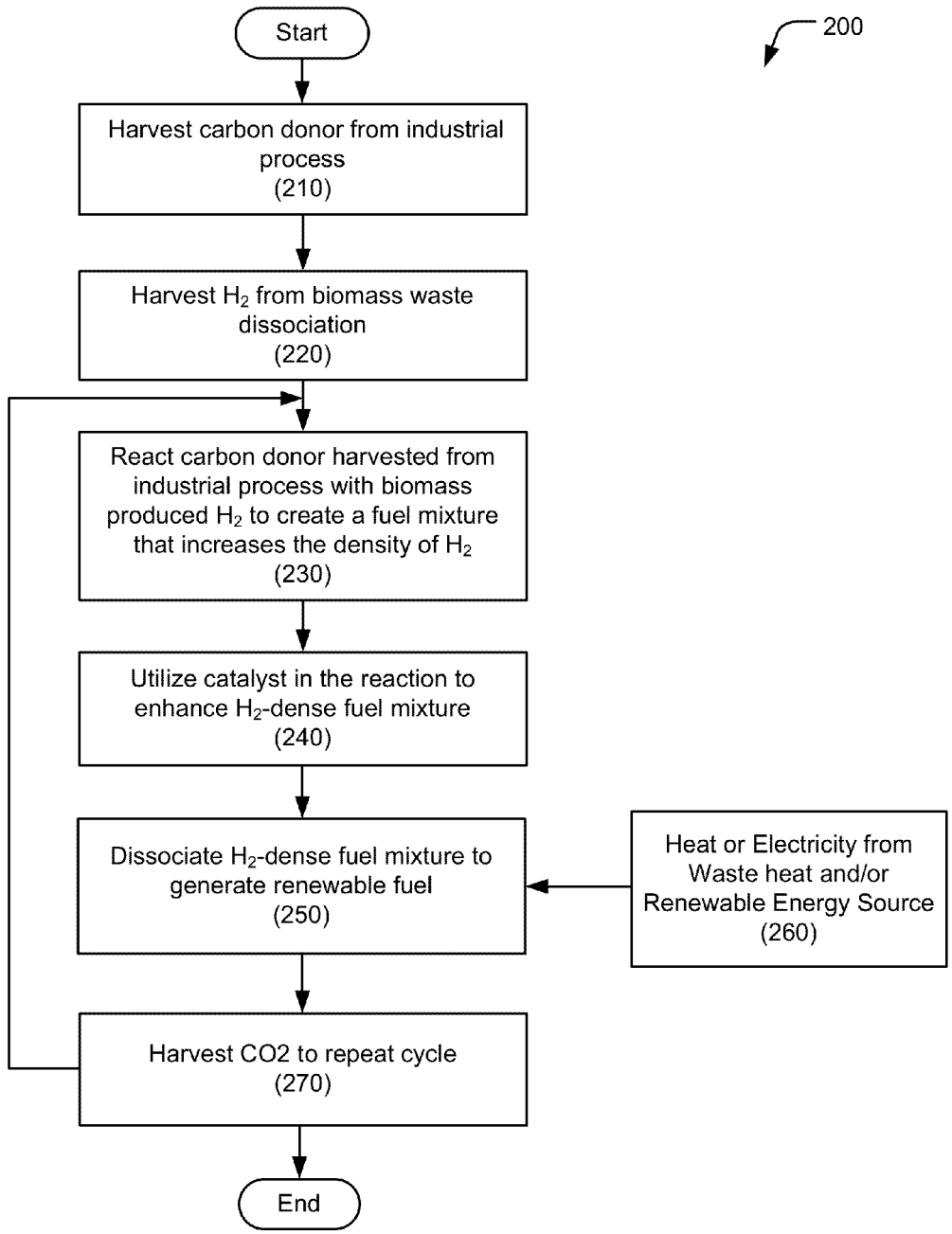
FIG. 2 is a process flow diagram of an exemplary process for generating oxidized fuel and hydrogen fuel by dissociating the $H_2$-dense fuel mixture generated by reacting repurposed or recycled $CO_2$ from industrial waste with hydrogen from biomass waste.

FIG. 2 is a process flow diagram of an exemplary process 200 for generating oxygenated fuel species and hydrogen fuel by dissociating the $H_2$-dense fuel mixture generated by reacting repurposed or recycled $CO_2$ from industrial waste with hydrogen from biomass waste. A system (e.g., system 300 below) harvests a carbon donor from industrial processes (210). The carbon donor, such as carbon dioxide or carbon monoxide used in the thermochemical regeneration described here can be harvested from readily available sources of $CO_2$, such as from breweries, bakeries, central power plants, coking, calcining, and/or operations that burn hydrocarbons. The system obtains hydrogen from biomass waste dissociation (220). The harvested $CO_2$ can be used to produce liquid feedstocks for production of chemicals and/or fuels by reacting with the biomass waste produced hydrogen (230). For example, the methanol fuel produced in the described thermochemical regeneration of $CO_2$ with $H_2$ can be used to power fuel cells and/or gasoline and diesel engines adapted to burn methanol in a non-polluting manner. U.S. Pat. No. 6,155,212 titled "METHOD AND APPARATUS FOR OPERATION OF COMBUSTION ENGINES" and U.S. Pat. No. 6,756,140 titled "ENERGY CONVERSION SYSTEM" describe apparatus and techniques for adapting gasoline and diesel engines to burn methanol, the entire contents of which are incorporated by reference. The methanol synthesis process summarized in Equations 1 and 2 may be implemented by various steps including catalytic synthesis at 95 to 100 atmospheres pressure and 500° F. (260° C.) (240). As described above, catalysts for the processes of Equations 1 and 2 can include copper-zinc-oxide and deposited sinter mixture of copper and copper-zinc oxide at various process synthesis conditions including about 260° C. (500° F.) and 1500 psi to produce methanol or methanol and water as shown.

As shown in illustrative Equations 5A, 5B, and 5C an alcohol such as ethanol or methanol or various mixtures of alcohols can be thermochemically reformed or dissociated in a second reaction with waste heat (e.g., reinvested or recycled from a solar dish or engine exhaust) and/or water to produce one or more oxides of carbon and hydrogen fuel (250).

$$C_2H_5OH + H_2O + \text{heat} \rightarrow 2CO + 4H_2 \quad \text{Equ 5A}$$

$$C_2H_5OH + H_2O + \text{heat} \rightarrow 2CO_2 + 6H_2 \quad \text{Eqn 5B}$$

$$CH_3OH + H_2O + \text{heat} \rightarrow CO + 3H_2 \quad \text{Eqn 5C}$$

Power and heat supplied by an engine, solar concentrator, or other ordinarily wasted or renewable sources can supply all or substantial portions of the energy or heat needed for the endothermic operations and processes for generating the renewable fuel, such as the H$_2$-dense fuel (260). By incorporating energy recovered from ordinarily wasted heat, the new fuel species produced by thermochemical regeneration can release 15 to 25% more energy upon combustion than the original alcohol feed stocks.

Similarly to Equations 5A, 5B and/or 5C, low-cost fuel and water mixtures, such as hydrocarbons and water with or without an emulsifier or an alcohol, such as methanol and water as shown in Equation 2 may be thermochemically reformed into new fuel species such as carbon dioxide and hydrogen for separation or direct use as a mixture for injection into the combustion chamber of an engine as shown in Equation 6.

$$CH_3OH + H_2O \rightarrow CO_2 + 3H_2 \qquad \text{Eqn 6}$$

This yields a much more powerful fuel—primarily hydrogen. This fuel can be utilized in a fuel cell or burned in an engine (to generate electricity and/or for transportation) and produce clean water as a byproduct as shown in Equation 7.

$$CO + 3H_2 + 2O_2 \rightarrow 3H_2O + CO_2 \qquad \text{Eqn 7}$$

The CO$_2$ byproduct can be harvested and repurposed or recycled in a reaction with hydrogen produced from biomass dissociation to continuously repeat the cycle (270).

Whereas hydrogen used in fuel-cell technology would typically require pure (and therefore is expensive to produce), hydrogen used in internal combustion engines can be impure. The described process of thermochemical regeneration is just as effective with impure or dirty hydrogen as it is with expensive, pure hydrogen. For example, hydrogen made from black water, organic wastes, or sewage has organic carbon as an impurity. However, just as the CO$_2$ is being prevented from becoming an atmospheric pollutant, hydrogen sourced from bio-wastes provides an additional benefit of reducing pollution from this inexpensive and sustainable resource. In each instance, potential energy, which would otherwise be lost as waste can be harvested and repurposed or recycled to generate renewable fuel.

Catalysts that improve the rate of the processes of Equations 6-7 can include transition metal carbides, borides, and nitrides including non-stoichiometric mixtures and/or intermetallic compounds with approximate formulas such as Fe$_3$C, Co$_3$C, Co$_3$Fe$_3$C$_2$, Mn$_3$C, FeC$_3$, CoC$_3$, CoFeC$_6$, MnFeC$_6$, Mn$_5$C$_2$, MnFeC$_6$, Fe$_3$Cr$_3$C$_2$, Fe$_3$Co$_2$BNC$_2$, Fe$_3$VC$_2$, Fe$_4$NC$_2$, Fe3MoC$_2$, and Fe$_5$BNC.

It may be desired to operate such processes cyclically with electrolysis being performed at times that electricity is inexpensive or when surplus electricity is available from intermittent magnitudes of renewable energy production. Thus a fluid product that has less density than the feedstock can be restricted from expansion until the pressure desired is achieved for storage, transmission by a fluid conduit, to generate heat by combustion or catalytic oxidation or for a chemical process such as a fuel cell or a regenerative electrolyzer/fuel cell or physical reaction including reactions that are aided by pressurization.

As an example, marine applications such as large cargo ship engines can be made to utilize a cheap petrochemical like paraffin with the resulting propulsion process producing clean water and hydrogen in storage by the end of the trip. By utilizing the power for transportation, the waste heat byproduct from the engines is used to drive the continuing thermochemical regeneration, improves overall efficiency and transforms wastes and pollutive products into energy carriers and productive energy. A vessel utilizing such technologies could be propelled while hydrogen or methanol is produced for fueling fuel cells, aircraft, missiles, unmanned reconnaissance probes, and new tactical weapons.

In another aspect, the techniques, apparatus and systems described herein readily accept solutions of water and fuels including oxygenated constituents. The ability to utilize solutions of water and fuels provides various advantages including: 1) saving energy needed to dry or remove water from oxygenated fuel constituents; 2) reducing fuel production cost by avoiding the equipment and energy expenses required to produce and store water-free fuels; 3) reducing toxicity by reducing or eliminating the concentration gradient between water solutions within living cells and the fuel-water solution; 4) and to facilitate beneficial thermochemical regeneration production of more energetic and faster burning hydrogen-characterized fuels (see Equations 8, 9, and or 10 below.)

Figure 3A:
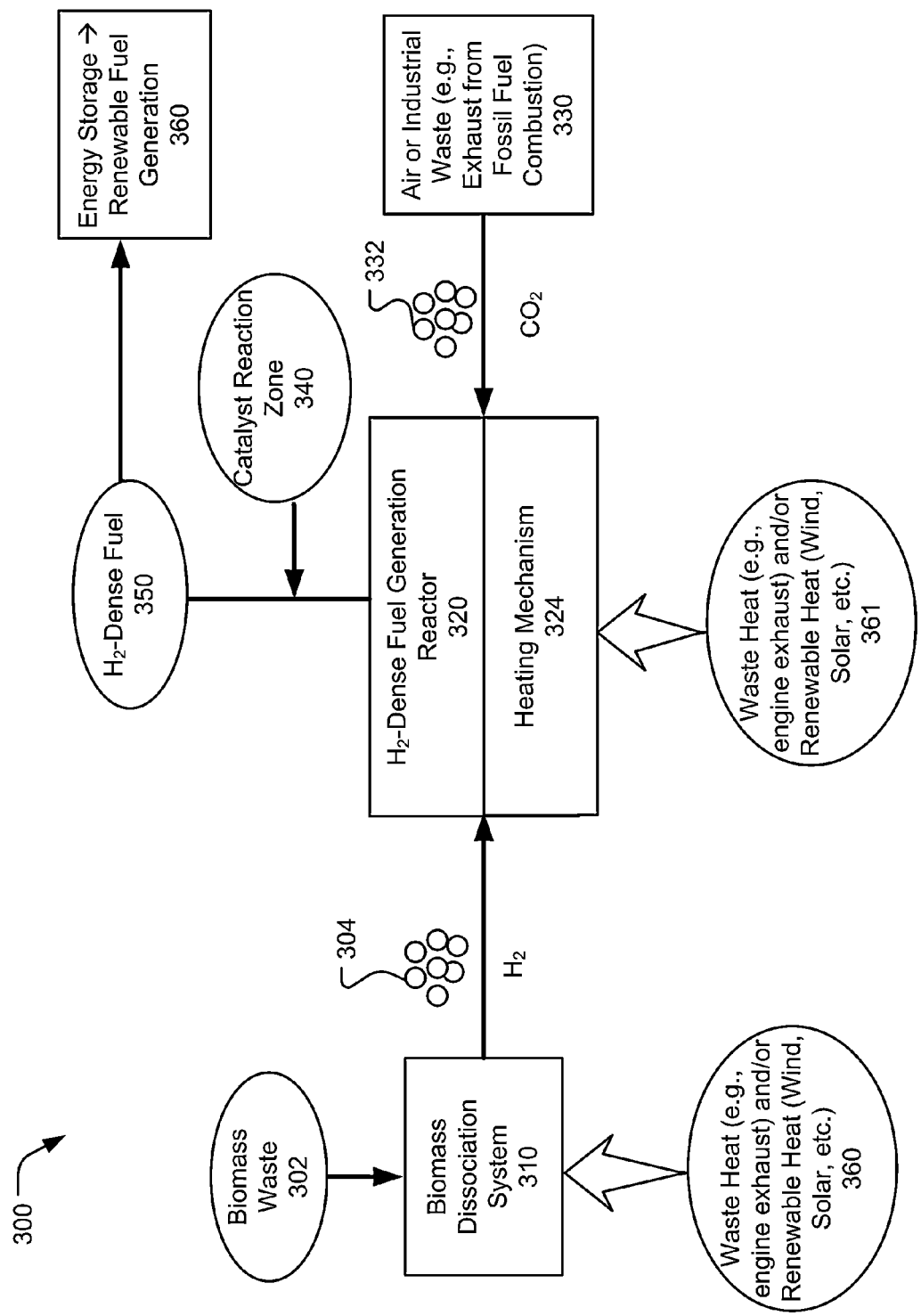
FIG. 3A is a block diagram showing an exemplary system for repurposing or recycling $CO_2$ harvested from industrial processes as waste to create renewable fuel by reacting with biomass produced hydrogen.

FIG. 3A is a block diagram showing an exemplary system 300 for repurposing or recycling CO$_2$ harvested from industrial processes as waste to create renewable fuel by reacting with biomass produced hydrogen. The system 300 includes a biomass dissociation system 310 that receives biomass waste 302 to be dissociated into carbon, hydrocarbons, alcohols, ammonia and hydrogen using a thermochemical regenerative process. The heat used to dissociate the biomass waste 302 can include waste heat 360, 361 from engine exhausts, engine cooling system etc. that otherwise would be released to the environment. Also, one or more of renewable energy sources, such as wind, solar, etc. can be used to generate the heat.

From the biomass dissociation system 310, low specific energy hydrogen 304 (from dissociation of hydrocarbons, for example) is captured and forwarded to H$_2$-dense fuel generating reactor 320, which includes a heating mechanism 324. The H$_2$-dense fuel generating reactor 320 also receives carbon donors, such as CO$_2$ 332 harvested from industrial processes 330 (e.g., exhaust gases from fossil fuel combustion or air). The H$_2$-dense fuel generating reactor 320 causes the low specific energy H$_2$ to react with the harvested carbon donors, such as CO$_2$ 332 to generate H$_2$-dense fuel 350, such as methanol. The carbon donors 332 can be obtained from air or industrial waste 330 (e.g., exhaust from fossil fuel combustion).

The system 300 can include a catalyst reaction zone 340 to receive one or more catalysts that enhances the generation of the H$_2$-dense fuel mixture. Examples of catalysts are described above.

The generated H$_2$-dense fuel mixture 350 is storable and transportable. Because the H$_2$-dense fuel mixture 350 carries H$_2$ fuel in a transportable form, the H$_2$-dense fuel mixture operates as a vehicle for carrying energy to a desired destination. The H$_2$-dense fuel 350 mixture can be dissociated to obtain H$_2$ fuel and oxygenated fuel species using a renewable fuel generation system 360.

Figure 3B:
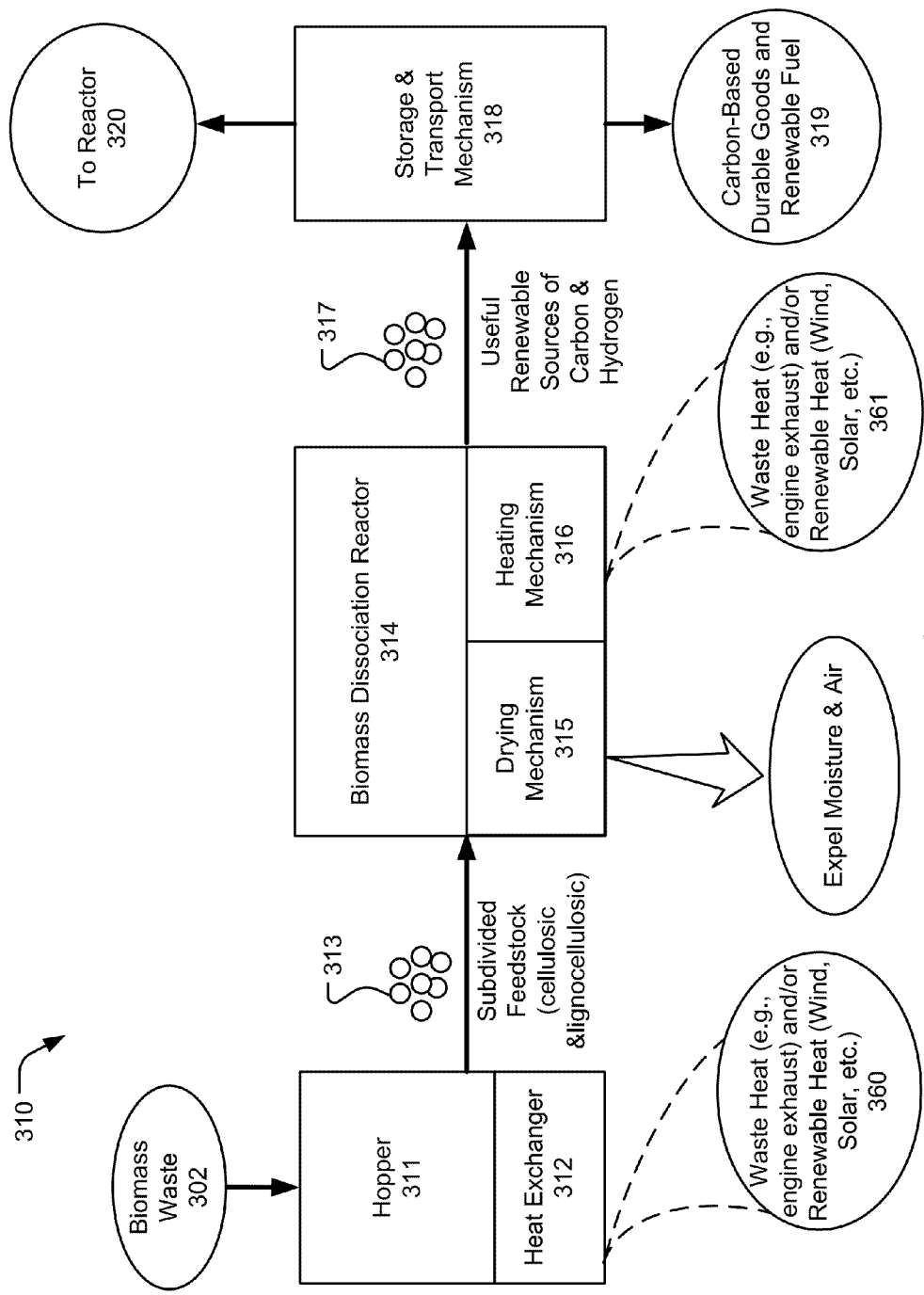
FIG. 3B is a block diagram showing an exemplary system for dissociating biomass waste into hydrogen and carbon carrying intermediaries.

FIG. 3B is a block diagram showing an exemplary system 310 for dissociating biomass waste into hydrogen and carbon carrying intermediaries. The system 310 includes a biomass waste intake component, such as a hopper 311 that receives the biomass waste 302 in raw form and breaks down (e.g., chips, chops, grinds, etc.) the raw material into subdivided feedstock, such as various energy crops and wastes including cellulosic and lignocellulosic materials. The hopper 311 can include a heating mechanism, such as a heat exchanger 312 to pre-heat the subdivided feedstock. The heat exchanger can recapture and recycle waste heat 360, 361 from an external heat source (e.g., a fuel cell, engine exhaust and/or renewable heat, such as wind, solar, etc.) or from biomass dissociation reactor 314 itself.

The subdivided (and in some implementations, pre-heated) feedstock 313 is forwarded to a biomass dissociation reactor 314 to dissociate the biomass waste feedstock into useful renewable sources of carbon and hydrogen, such as various hydrocarbons, alcohols, ammonia, and oxides of carbon. The reactor can include a drying mechanism 315 to expel moisture and air from the feedstock. The drying mechanism 315 can include an extruding device to physically 'squeeze out' the moisture and air from the feedstock. Examples of the extruding device include a helical screw conveyer and a ram piston conveyer. Also, the drying mechanism 315 can include one or more heating mechanisms, such as heat exchangers that capture heat generated by the reactor 314 and recycle the captured heat to dry the feedstock. The heat exchangers can also recapture and recycle waste heat 360, 361 from an external heat source (e.g., engine exhaust and/or renewable heat, such as wind, solar, etc.)

The reactor 314 can also include a heating mechanism 316 for generating adequate heat used in an anaerobic reaction to dissociate the biomass waste feedstock into the useful renewable sources of carbon and hydrogen 317, such as hydrocarbons, alcohols, ammonia and oxides of carbon. The generated useful renewable sources of carbon and hydrogen 317 can be forwarded to a storage and/or transport mechanism 318 to be used by the H2-dense fuel generation reactor 320 and in additional reactions to generate renewable fuel and/or carbon-based durable goods 319 as described in the U.S. patent application Ser. No. 13/027,068, now issued as U.S. Pat. No. 8,318,997, entitled "CARBON-BASED DURABLE GOODS AND RENEWABLE FUEL FROM BIOMASS WASTE DISSOCIATION," the entire contents of which is incorporated by reference. Moreover, the storage and/or transport mechanism 318 allows for efficient transport of the useful renewable sources of carbon and hydrogen 317 to remote locations for further processing.

The biomass dissociation reactor 314 can be configured to increase the thermal efficiency of the biomass waste conversion process while reducing or eliminating carbon dioxide formation. For example, the biomass dissociation reactor 314 can include mechanisms to perform various countercurrent drying (e.g., recycling heat) and elimination of air, moisture, and other oxygen donors prior to extraction of carbon, hydrocarbons such as methane, and/or hydrogen.

Figure 3C:
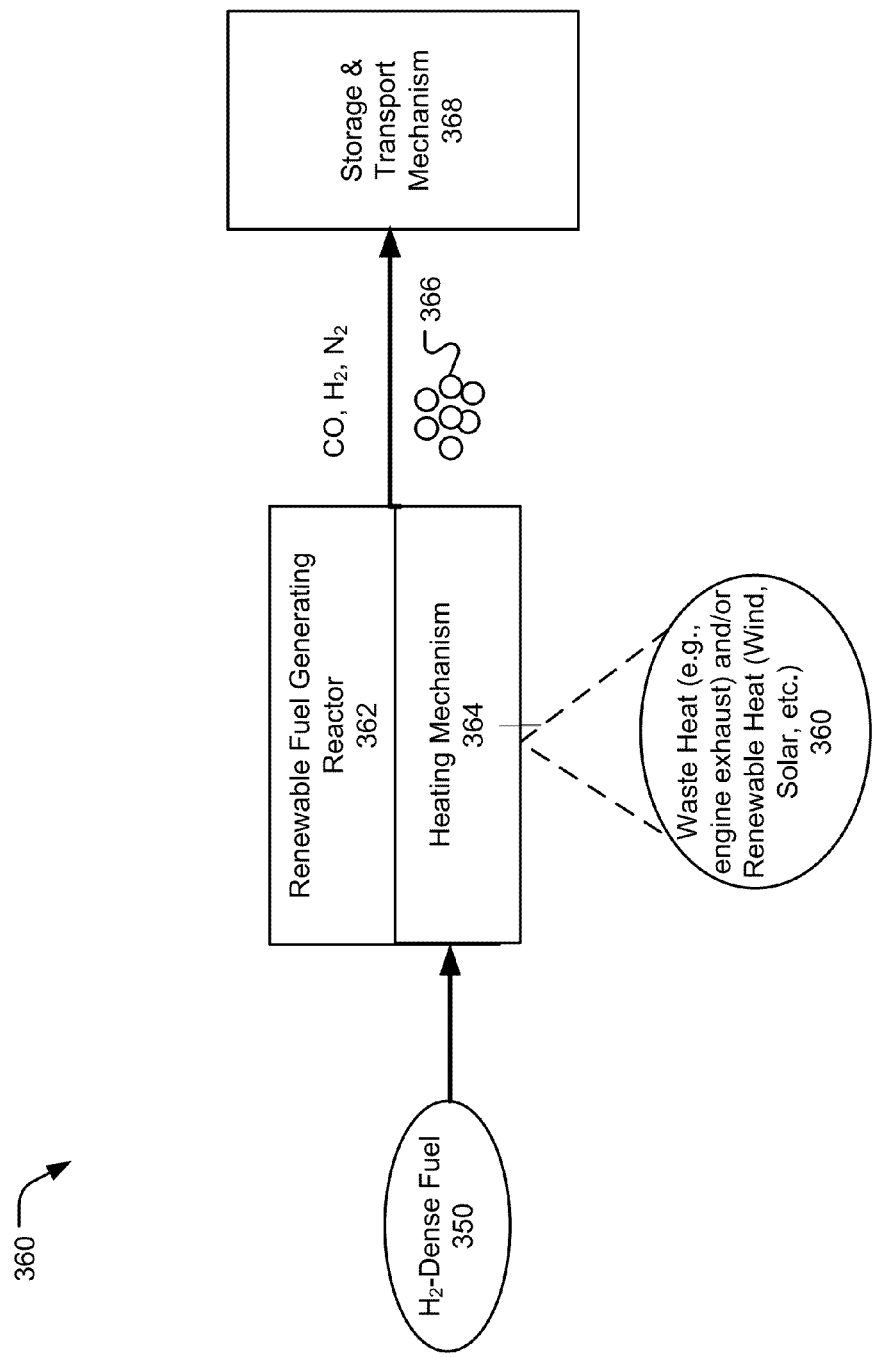
FIG. 3C is a block diagram showing an exemplary system for generating multi-purpose $H_2$-dense fuel for isolating hazardous contaminants and for storing energy as described above.

FIG. 3C is a block diagram showing an exemplary system 360 for generating multi-purpose $H_2$-dense fuel 350 for isolating hazardous contaminants and for storing energy as described above. The system 360 includes a renewable fuel generating reactor 362 that receives the $H_2$-dense fuel 350 generated as described above. The renewable fuel generating reactor 362 can include a heating mechanism 364 to apply heat necessary to covert the $H_2$-dense fuel mixture into renewable fuel and nutrients 366, such as oxides of carbon, hydrogen, and nitrogen. The heat used in the reaction can be obtained from waste heat from engine exhaust or cooling system that otherwise would be released to the environment. Also, heat from one or more renewable resources, such as wind, solar, running water, geothermal, etc. can be used in the reaction. In addition, the generated renewable fuel can be stored and/or transported to other locations using storage and transport mechanism 368, such as a pressurized container or pipelines.

Figure 4:
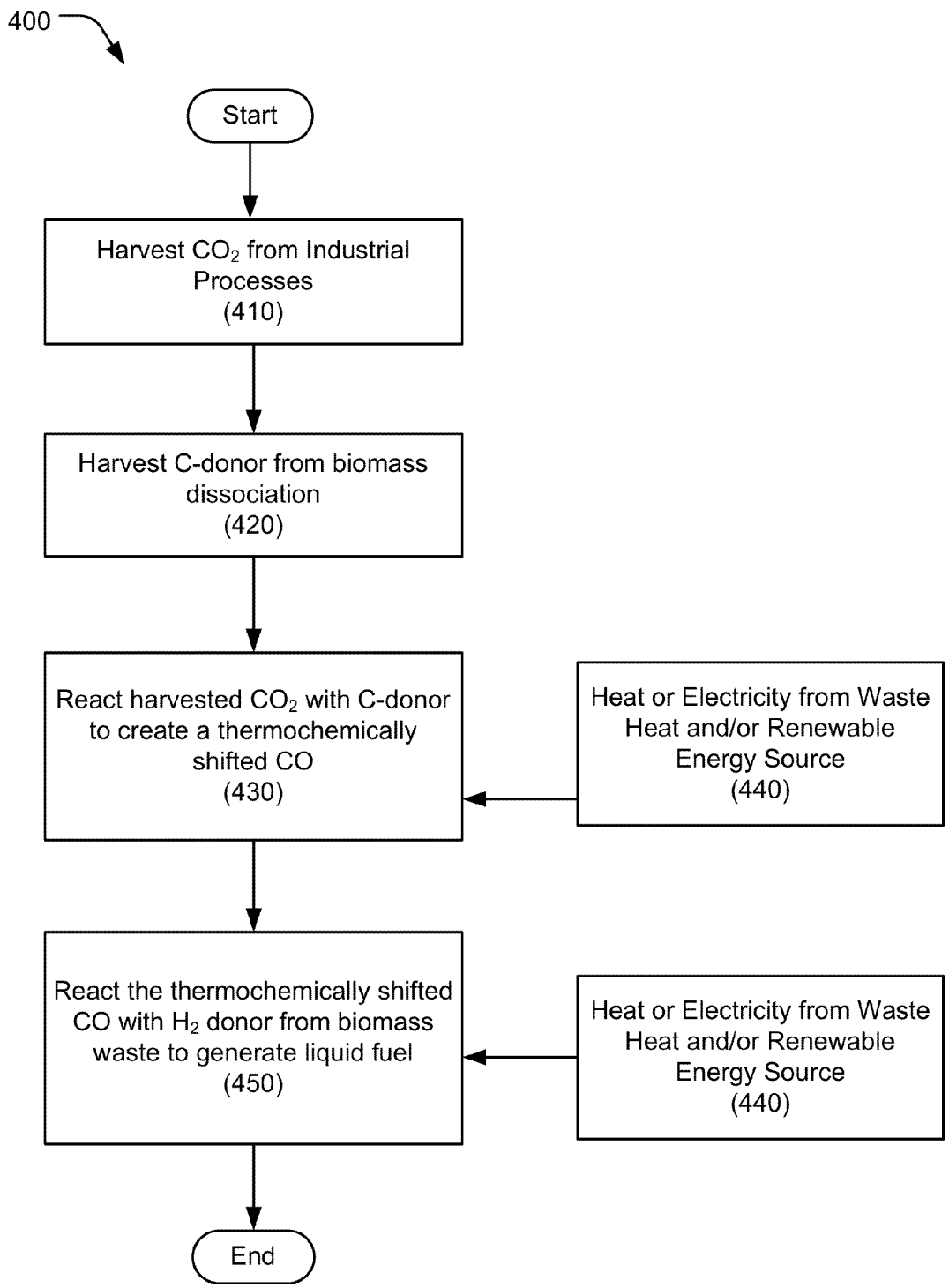
FIG. 4 shows a process flow diagram for a process for using harvested $CO_2$ (e.g., from fossil fuel combustion waste) as a source of thermochemically shifted CO by reacting the fossil produced carbon dioxide with a renewable carbon donor.

FIG. 4 shows a process flow diagram for a process 400 for using harvested $CO_2$ (e.g., from fossil fuel combustion waste) as a source of thermochemically shifted CO by reacting the fossil produced carbon dioxide with a renewable carbon donor. A system (e.g., system 500 below) can collect $CO_2$ from industrial processes including bakeries, breweries, calcining plants, and other sources such as power plants, fuel cells and engines that use carbonaceous fuels (410). Carbon monoxide may also be provided by the process summarized in Equation 8 for methanol producing processes such as those generally depicted by Equation 1 above. The system can obtain a carbon donor produced by the hydrocarbon (produced from biomass waste) dissociation processes summarized in Equations 3 and 4 above (420). The carbon donor from hydrocarbon dissociation can be reacted with the harvested $CO_2$ in presence of adequate heat to produced thermochemically shifted CO (430) as shown in Equation 8 below.

$$CO_2+C+ENERGY \rightarrow 2CO \qquad \text{Eqn 8}$$

The carbon donor for this purpose may also be delivered and donated by utilizing condensable liquid fuel constituents such as methanol to be reacted with harvested $CO_2$. It can be advantageous to utilize a renewable energy resource (e.g., methane from biomass) to provide carbon for processing carbon dioxide into carbon monoxide as shown in Equation 9.

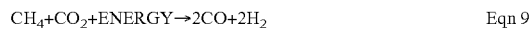

$$CH_4+CO_2+ENERGY \rightarrow 2CO+2H_2 \qquad \text{Eqn 9}$$

The heat used in the reaction of the harvested $CO_2$ with the biomass waste generated carbon donor can include waste heat from engine exhausts, engine cooling system etc. that otherwise would be released to the environment (440). Also, one or more of renewable energy sources, such as wind, solar, etc. can be used to generate the heat.

Higher pressure hydrogen can be used to pressurize the products of Equation 9, such as carbon monoxide and hydrogen. Also, the higher pressure hydrogen can be produced by other energy induced dissociations including electrolysis of anaerobically developed acids and liquors from organic digestion processes and from water as generally shown in Equations 3, 4, 10 and 11.

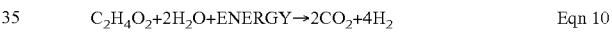

$$C_2H_4O_2+2H_2O+ENERGY \rightarrow 2CO_2+4H_2 \qquad \text{Eqn 10}$$

$$H_2O+ENERGY \rightarrow 0.5O_2+H_2 \qquad \text{Eqn 11}$$

Pressurized hydrogen or pressurized and heated hydrogen such as may be produced by the pressurizing processes shown in Equations 3, 4, 10, and or 11 can be added to pressurize the products of Equation 9 to form a desired compound such as DEE, DME fuel or an alcohol such as methanol as shown in Equation 12 (450).

$$CO+H_2+H_2 \rightarrow CH_3OH \qquad \text{Eqn 12}$$

Liquid fuel such as methanol provided by the processes summarized in Equations 1 and 12 can readily be stored, transported, metered and dispensed by equipment and systems typically utilized for diesel, gasoline, and other alcohol fuels.

Equation 13 shows the process steps of dissociating carbon monoxide such as carbon monoxide from processes summarized in Equation 5 or from other sources to provide partial oxidation of methane to produce methanol and/or DME.

$$CH_4+CO+ENERGY \rightarrow CH_3OH+C \qquad \text{Eqn 13}$$

The process summarized in Equation 13 may be performed on or in the presence of activated carbon and the carbon produced as oxygen that is utilized to form methanol may be precipitated to add to the inventory of such carbon. Facilitation of the reaction may be provided by a reactor that utilizes activated carbon to adsorb carbon monoxide that is dissociated with or without the aid of catalysts to release oxygen that partially oxidizes methane to form methanol.

The heat used in the reaction of the harvested $CO_2$ with the biomass waste generated carbon donor can include waste heat from engine exhausts, engine cooling system etc. that otherwise would be released to the environment (440). Also, one or more of renewable energy sources, such as wind, solar, etc. can be used to generate the heat.

Repurposing or recycling of oxides of carbon such as carbon dioxide or carbon monoxide from air-burning processes generally poses the problem of separation or accommodation of nitrogen contamination. Another process variation for preparation of values from mixtures of reactive ionic species is provided by arc, corona, microwave, or radiative ionization. Mixtures of carbon monoxide, including production by the process of Equation 5, and hydrogen including production by the process of Equations 3 or 4, and such nitrogen are reacted to produce $CH_3OH$ and $NH_3$ as shown in Equation 14.

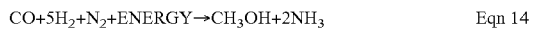

$$CO+5H_2+N_2+ENERGY \rightarrow CH_3OH+2NH_3 \qquad \text{Eqn 14}$$

Ammonia ($NH_3$) produced by this or other reactions that utilize hydrogen produced by the processes typical to Equations 3 or 4, can be safely stored and conveyed. This provides compact storage and may serve as a precursor of hydrogen. Ammonia can be stored in various ways including as a pressurized liquid, a salt such as ammonium chloride, or in activated media such as carbon and pressurization can be accomplished by heat addition. Decomposition of ammonia as it passes a catalyst may be utilized to pressurize the $N_2$ and $H_2$ products including pressurization of carbon monoxide and hydrogen that may be co-produced from methanol or wet methanol.

Figure 5:
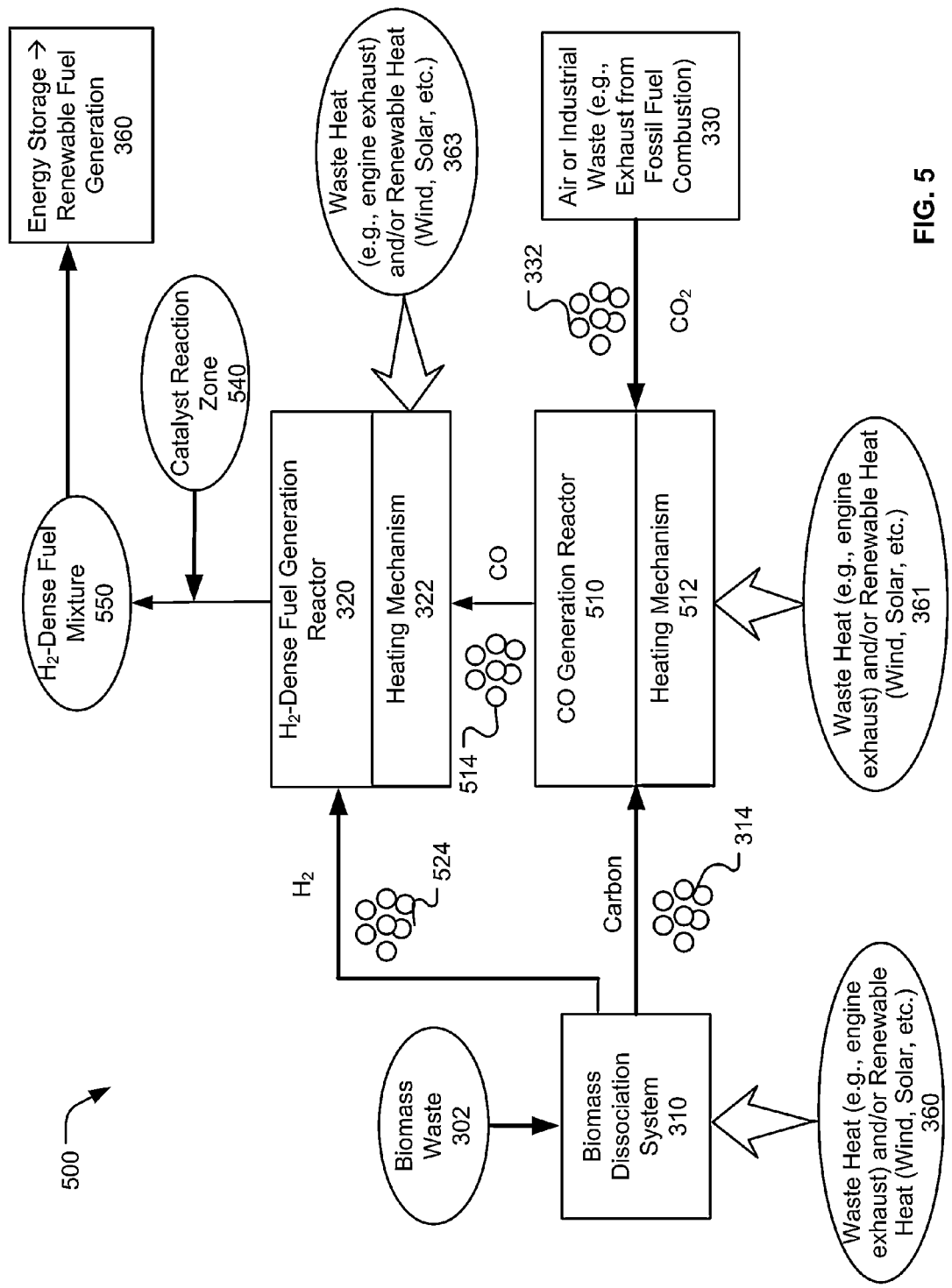
FIG. 5 is a block diagram of an exemplary system for generating renewable fuel from thermochemically shifted CO reacted with hydrogen from biomass waste dissociation.

FIG. 5 is a block diagram of an exemplary system 500 for generating renewable fuel from thermochemically shifted CO reacted with hydrogen from biomass waste dissociation. The system 500 includes a biomass dissociation system 310 that receives biomass waste 302 to be dissociated into carbon, hydrocarbons, alcohols, ammonia and hydrogen using a thermochemical regenerative process. The heat used to dissociate the biomass waste 302 can include waste heat 360, 361, 363 from engine exhausts, engine cooling systems, etc. that otherwise would be released to the environment. Also, one or more of renewable energy sources, such as wind, solar, etc. can be used to generate the heat.

From the biomass dissociation system 310, carbon donor 314 (from dissociation of hydrocarbons, for example) is captured and forwarded to a CO generating reactor 510, which includes a heating mechanism 512. The carbon donor 314 is reacted with $CO_2$ 332 harvested from industrial processes 330 (e.g., exhaust gases from fossil fuel combustion or air). The CO generating reactor 510 can cause the carbon donor to react with the harvested $CO_2$ 332 obtained from air or industrial processes (e.g., exhaust from fossil fuel combustion, waste stream of a polymer plant, etc.) to generate CO 514.

The thermochemically shifted CO 514 is forwarded to a $H_2$-dense fuel generating reactor 320, which includes a heat exchange mechanism 322. Depending upon the temperatures and pressures of the reactants entering 320, the system insulation and heat loss or gain in reactor 320, the process may have an overall endothermic or exothermic process characterization. The $H_2$-dense fuel generator 320 also receives hydrogen donors 524 harvested from biomass waste dissociation system 310. The $H_2$-dense fuel generating reactor 320 can cause the hydrogen donors 524 (e.g., low specific energy $H_2$) to react with the shifted CO 514 to generate $H_2$-dense fuel 550, such as methanol. The heat sourced or used to generate the $H_2$-dense fuel mixture 550 can include waste heat from engine exhausts, engine cooling systems, etc. that otherwise would be released to the environment. Also, one or more of renewable energy sources, such as wind, solar, running water, geothermal, etc. can be used to generate the heat. Exothermic heat removed may be used to improve the productivity of anaerobic digestion operations.

The system 500 can include a catalyst reaction zone 540 to receive one or more catalysts that enhances the generation of the $H_2$-dense fuel mixture. Examples of catalysts are described above.

The generated $H_2$-dense fuel mixture 550 is storable and transportable. Because the $H_2$-dense fuel mixture 550 carries $H_2$ fuel in a transportable form, the $H_2$-dense fuel mixture operates as a vehicle for carrying energy to a desired destination. The $H_2$-dense fuel 550 mixture can be dissociated to obtain $H_2$ fuel and oxygenated fuel using a renewable fuel generation system 360.

Figure 6:
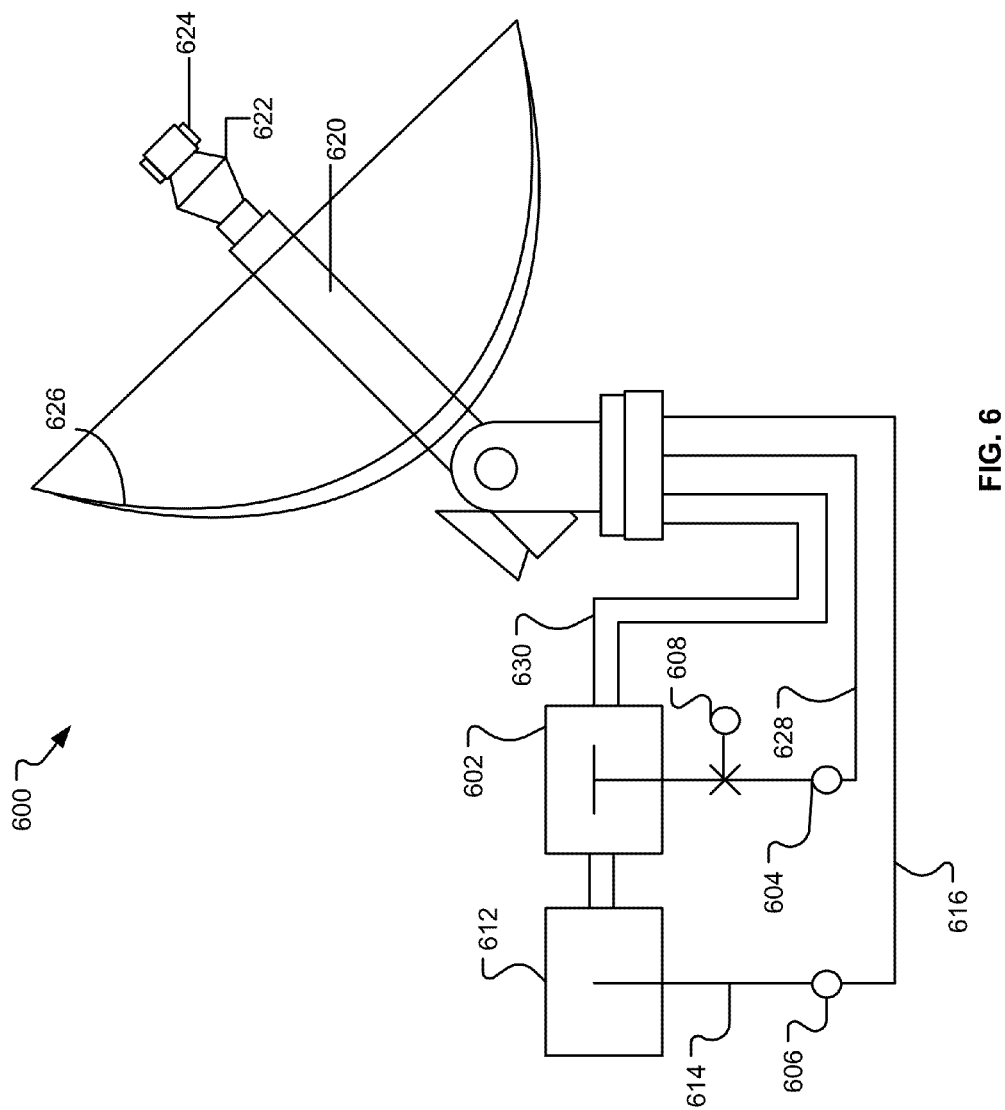
FIG. 6 is a block diagram of an exemplary system for repurposing or recycling carbon and hydrogen.

FIG. 6 is a block diagram of an exemplary system 600 for repurposing or recycling carbon and hydrogen. Hydrogen generated from hydrocarbon dissociation as in Equation 1 can be used in an engine 602 such as a gas turbine or positive displacement engine such as a rotary combustion or piston engine and the output of the engine can be applied to a load such as a pump or generator 612 as shown. The exhaust from the engine 602 may be used as a heat supply for the endothermic reactions previously disclosed and or it may be delivered through conduit 630 to a heat exchanger 620 for receiving heat from a suitable source such as provided by solar concentrator 626 which may be of any suitable design including a radiation trap by selective surface and/or one or more selectively transmissive glazings, and/or concentrators such as a trough, dish, or a Fresnel lens. Hydrogen may be supplied by pipeline 604 including arrangements for subterranean delivery of relatively pure hydrogen from an industrial park that produces durable goods from carbon as shown in Equation 1 or hydrogen may be interchangeably delivered in a mixture with other fuels such as natural gas or various producer gas mixtures.

The exhaust from the engine 602 may source heat for various other purposes including the previously described endothermic processes and a portion of the exhaust may be further heated by the solar concentrator 626 to provide high temperature gas for expansion in an engine such as a turbine 622 and the output of such work production may be applied to a pump or generator 624. Electricity produced by generator 624 may be delivered through a cable 616 for distribution by a collector cable 606 as electricity delivered to 606 through 614 from generator 612. Fuel from pipe 604 may be delivered by line 628 and controlled by a pump or valve 608 for combustion in engine 622 for operation at times insufficient solar energy is available to enable the system to meet demands for electricity.

Depending upon demand for power and available solar energy, additional working fluid such as air or water may be delivered to a conduit 630 to provide peaking power by maximizing the output of the solar collector 626 and the engine 622.

Carbon Harvesting from Agricultural Processes

Industrial processes in populated areas are not solely responsible for the production and emission of greenhouse gases, such as carbon dioxide, methane, and nitrous oxide; as farming and other agricultural processes can also be significant producers of these harmful wastes that can be recycled and repurposed to generate renewable fuel, such as methanol fuel. Rather than waste carbon by taking carbon out of carbon dioxide ($CO_2$), for example, the described techniques repurpose or recycle $CO_2$ in reactions with waste-produced hydrogen to generate renewable fuel. Techniques, apparatus and systems are described for implementing thermochemical regeneration reactions in which carbon donors are harvested from agricultural processes.

Figure 7A:
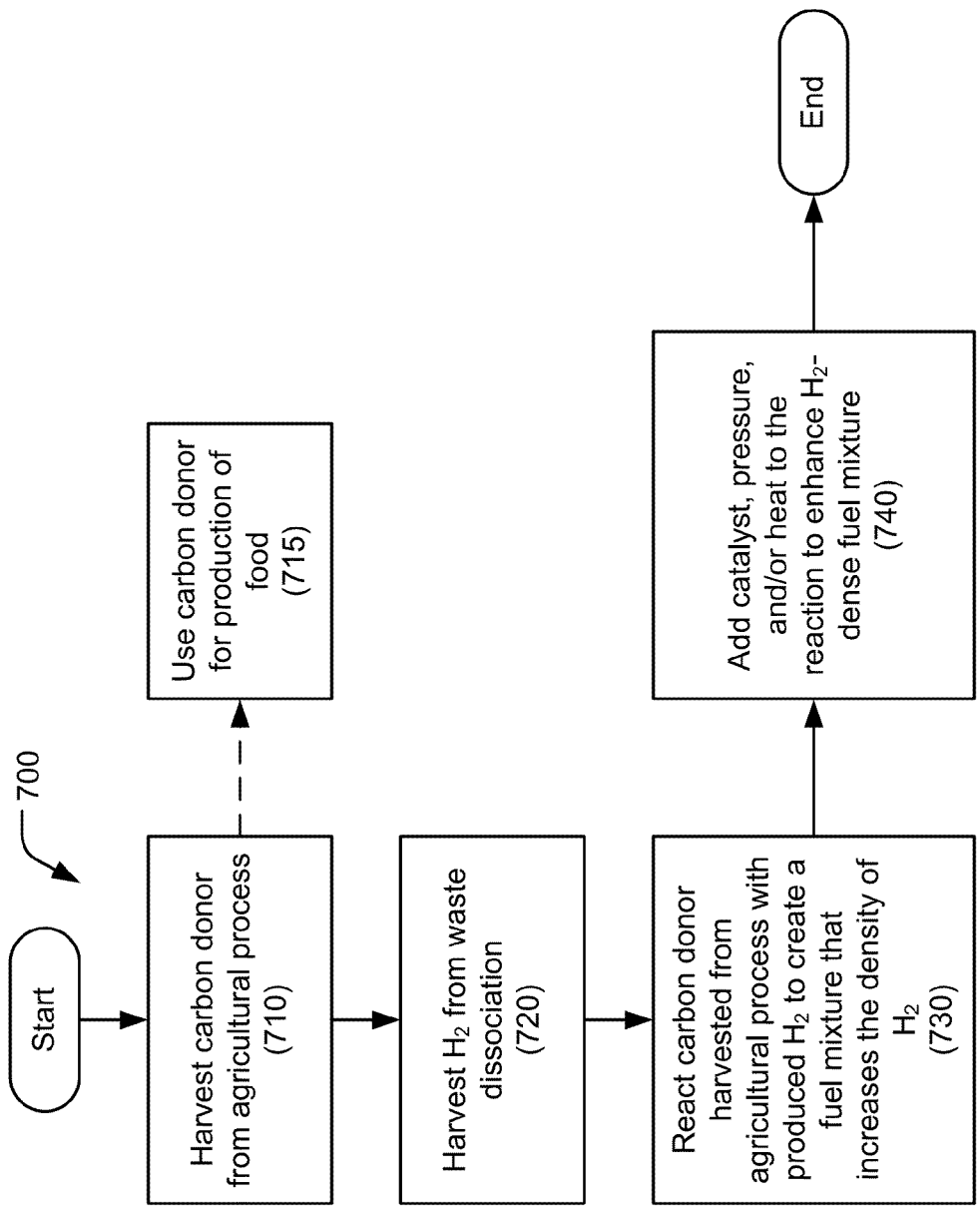
FIG. 7A shows an exemplary process flow diagram for synthesizing a hydrogen-dense fuel mixture derived from reinvesting, repurposing or recycling carbon donors harvested from agricultural processes waste.

FIG. 7A shows a process flow diagram of an exemplary process 700 for reinvesting, repurposing or recycling carbon donors harvested from waste generated by agricultural processes to react with hydrogen from a general waste dissociation process to synthesize a renewable fuel mixture that increases the density of hydrogen. In this exemplary process 700, a carbon donor, such as $CO_2$, carbon monoxide (CO), and/or methane ($CH_4$), can be harvested from agricultural processes (710) with readily available agricultural sources of carbon substances. For example, agricultural processes with wastes and other sources of carbon substances can include landfills (e.g., landfill gas emission and migration), microbial respiration, carbon-based gas efflux and trace mineral release from soil, and degradation of the permafrost. Other examples of wastes that can be dissociated to harvest carbon donors in process 710 can include the dehydrogenation of carcinogenic materials, which in addition to providing carbon that can be reinvested, recycled or repurposed for fuel and materials, can also render a carcinogenic substance inactive post dehydrogenation.

Such processes for converting wastes into hydrogen and carbon to make higher value durable goods instead of burning the carbon provide much greater productivity and new product offerings for industrial processes particularly including farming. Co-produced hydrogen can be reacted with concentrated supplies of carbon dioxide from anaerobic farm waste digesters, an/or by bakeries, breweries, calciners and power plants to make liquid fuel alcohols such as methanol, ethanol, or dimethyl ether or diethyl ether and these liquid fuels can be stored in conventional gasoline or diesel fuel tanks to achieve the net impact on the environment of being no more than burning hydrogen in fuel cells and/or converted gasoline or diesel engines.

Hydrogen ($H_2$) can be harvested from a waste dissociation process (720), such as from hydrocarbon dissociation to generate hydrogen (as described in Equations 3-4). For example, hydrogen can be derived from dissociation of hydrocarbon compounds found in biomass waste; waste streams from energy utilization including at least one of wind, hydro, biomass, solar, tidal, geothermal, and nuclear or coal power plants; pipelines transporting hydrogen; and electrolytic splitting of water. In other examples, hydrogen can be harvested from dehydrogenation of agricultural process wastes, such as the release of soil nutrients and trace minerals, like ammonia. The harvested carbon donors can be used to produce fuels and materials (including durable goods) by reacting with the waste-produced hydrogen (730); such produced fuels can include fuel mixtures that increase the density of hydrogen. For example, an alcohol such as methanol fuel can be produced in the described thermochemical regeneration of $CO_2$ with $H_2$ (as described in Equations 1-2), which can be used in a multitude of applications including powering gasoline and diesel engines adapted to burn methanol in a non-polluting manner.

The exemplary fuel mixture with high hydrogen density produced in process 730 can be further processed by adding a catalyst and increasing pressure and heat (740). For example, the methanol synthesis process summarized in Equations 1 and 2 can be implemented by various steps including adding a catalyst to the reaction(s) and/or increasing pressure (e.g., to 95 to 100 atmospheres) and heat (e.g., to 500° F. (260° C.)). In some instances, a catalyst can replace pressure to facilitate the reaction. In other instances, the reaction in forming the renewable fuels can be carried out without a catalyst. Carrying out the synthesis reaction with the addition of a catalyst and additional pressure and heat can be desired. In such an example, catalysts for the processes of Equations 1 and 2 can include copper-zinc-oxide and deposited sinter mixture of copper and copper-zinc oxide at various process synthesis conditions including about 260° C. (500° F.) and 1500 psi to produce methanol or methanol and water as shown.

In addition to dissociation of hydrogen donor wastes, hydrogen can also be harvested in 720 by electrolytic splitting of water using any clean, alternative energy source, where hydrogen gas resulting from that process can be the hydrogen donor waste harvested in 720 and reacted in 730. Also, hydrogen can be derived from a non-$CO_2$ producing anaerobic dissociation of organic materials and/or by utilization of energy sources such as wind, hydro, biomass, solar, tidal, geothermal, or off-peak nuclear power plants. Hydrogen can also be produced from virtually any biomass waste that ordinarily rots or burns. Carbon-neutral liquid compounds for storage of hydrogen can be synthesized from hydrogen and carbon dioxide. Also, hydrogen may be produced at or near the site or delivered from pipelines that are transporting hydrogen.

In another aspect of process 700, the harvested carbon donor(s), such as $CO_2$, can be extracted from process 710 and can be used in the production of food (process 715), such as in photosynthetic processes of algae (in hydroponics) for food uses. Another example can include (also in the case of $CO_2$) the harvested carbon donors extracted from process 710 being used to produce feedstocks in the production of chemicals.

Figure 7B:
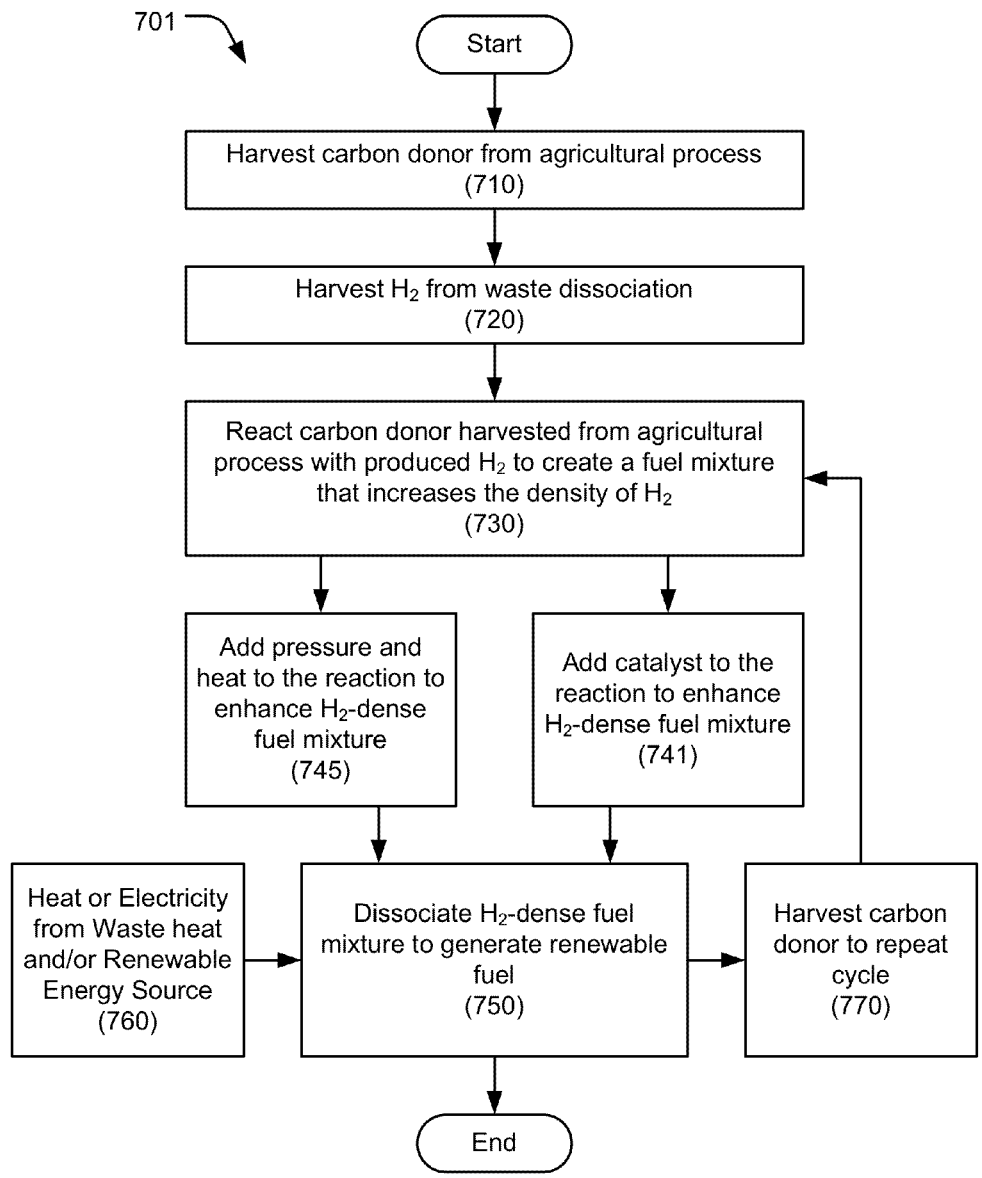
FIG. 7B shows another exemplary process flow diagram for synthesizing a renewable fuel dissociated from a hydrogen-dense fuel mixture derived from reinvesting, repurposing or recycling carbon donors harvested from agricultural processes waste.

FIG. 7B shows a process flow diagram of another exemplary process 701 for reinvesting, repurposing or recycling carbon donors harvested from waste generated by agricultural processes to react with hydrogen from a general waste dissociation process to synthesize a renewable fuel dissociated from the hydrogen-dense fuel mixture. In this exemplary process 701, a carbon donor (such as $CO_2$, CO, and/or $CH_4$), can be harvested from agricultural processes (710) with readily available agricultural sources of carbon substances, such as landfill emissions, microbial respiration, efflux from soil, and degradation of the permafrost. In some cases, the harvested carbon donors can also be used to produce feedstocks in the production of foods and/or chemicals, such as in process 715 described in FIG. 7A. In other cases, the harvested carbon donors from process 710 can be reacted with hydrogen harvested from a waste dissociation processes in process 720, which can result in the production of fuels, fuel mixtures, and other materials (process 730). Process 720 can include the dissociation of hydrocarbon to generate hydrogen (as described in Equations 3-4). The synthesized fuel mixture with high hydrogen density can be formed in some instances with a catalyst (741). In other instances, the synthesized fuel mixture with high hydrogen density can be formed with addition of pressure and/or heat (745). Also, the synthesis process can be implemented by various steps including adding a catalyst to the reaction(s) and/or increasing pressure and heat (740), described in FIG. 7A.

The synthesized $H_2$-dense fuel mixture of processes 740, 741, or 745 can be thermochemically reformed or dissociated in another reaction with waste heat (such as reinvested or recycled heat from a solar dish or engine exhaust) and/or electricity, along with water, to produce renewable fuels (for example, carbon oxides and hydrogen fuel) (750), as exemplified in Equation 5 using synthesized methanol. Power and heat supplied by an engine, solar concentrator, or other ordinarily wasted or renewable sources can supply the energy or heat (760) needed for the endothermic operations and processes for generating the renewable fuel (in 750), such as the $H_2$-dense fuel. By incorporating energy recovered from ordinarily wasted heat, the new fuel species produced by thermochemical regeneration can release 15 to 25% more energy upon combustion than the original alcohol feed stocks. Other embodiments of process 760 can utilize renewable energy sources to generate the heat and/or electricity to incorporate into process 750, including at least one of a wind energy generator, a solar energy generator, a hydro energy generator, and a geothermal energy generator.

Similarly to Equations 5A, 5B, and 5C, low-cost fuel and water mixtures, such as hydrocarbons and water with an emulsifier and a waste carbon donor and/or an alcohol or ether compound such as methanol and water as shown in Equation 2 can be thermochemically reformed into new fuel species such as carbon dioxide and hydrogen for separation or direct use as a mixture for injection into the combustion chamber of an engine as shown in Equation 6. This yields a much more powerful fuel—primarily hydrogen—where its original constituents can be derived from the waste of agricultural processes. This fuel can be burned in an engine (to generate electricity and/or for transportation) and produce clean water as a byproduct as shown in Equation 7. The $CO_2$ byproduct, for example, can be harvested and repurposed or recycled in a reaction with the waste-produced hydrogen to continuously repeat the cycle (770). Catalysts that improve the rate of the processes of Equations 6-7 can include transition metal carbides, borides, and nitrides including non-stoichiometric mixtures and/or intermetallic compounds with approximate formulas such as $Fe_3C$, $Co_3C$, $Co_3Fe_3C_2$, $Mn_3C$, $FeC_3$, $CoC_3$, $CoFeC_6$, $MnFeC_6$, $Mn_5C_2$, $MnFeC_6$, $Fe_3Cr_3C_2$, $Fe_3Co_2BNC_2$, $Fe_3VC_2$, $Fe_4NC_2$, $Fe3MoC_2$, and $Fe_5BNC$.

Figure 8A:
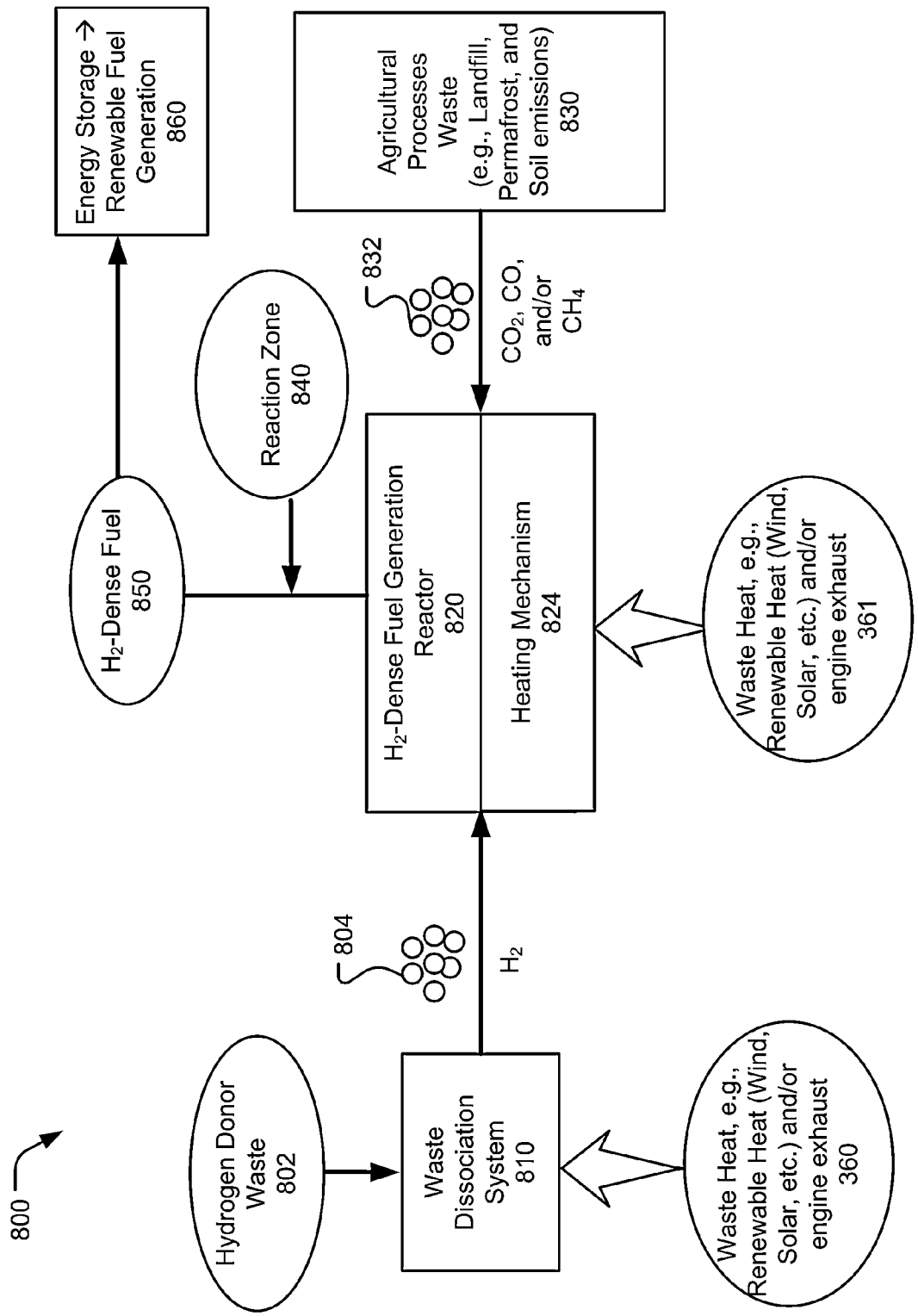
FIG. 8A shows a block diagram of an exemplary system for repurposing or recycling carbon donors harvested from agricultural processes waste to create renewable fuel by reacting with waste-produced hydrogen.

FIG. 8A shows a block diagram of an exemplary system 800 for repurposing or recycling carbon donors (such as $CO_2$, CO, and $CH_4$) harvested from agricultural processes as waste to create renewable fuel by reacting with waste-produced hydrogen. The system 800 includes a waste dissociation system 810 that receives hydrogen donor waste 802 from a waste stream, for example a biomass waste to be dissociated into carbon, hydrocarbons, alcohols, ammonia and hydrogen using a thermochemical regenerative process. The heat used to dissociate the hydrogen donor waste 802 can include waste heat 360, 361 from engine exhausts, engine cooling systems, etc. that otherwise would be released to the environment. Also, one or more of renewable energy sources, such as wind, solar, etc., can be used to generate the heat. The dissociated intermediaries and byproducts from waste dissociation system 810 can be generated into carbon-based durable goods, as described in the U.S. patent application Ser. No. 13/027,068, now issued as U.S. Pat. No. 8,318,997, entitled "CARBON-BASED DURABLE GOODS AND RENEWABLE FUEL FROM BIOMASS WASTE DISSOCIATION," the entire contents of which is incorporated by reference.

From the waste dissociation system 810, low specific energy hydrogen 804 (from dissociation of hydrocarbons, for example) can be captured and forwarded to $H_2$-dense fuel generating reactor 820, which includes a heating mechanism 824. The $H_2$-dense fuel generating reactor 820 also can receive carbon donors, such as $CO_2$, CO, and/or $CH_4$ (832), harvested from agricultural processes waste 830 from agricultural sources (e.g., gas emissions from landfills, permafrost degradation, and soil efflux). The $H_2$-dense fuel generating reactor 820 can also receive carbon donors harvested from industrial processes (e.g., exhaust gases from fossil fuel combustion or air), as well. The $H_2$-dense fuel generating reactor 820 causes the low specific energy $H_2$ to react with the harvested carbon donors such as $CO_2$, CO, and/or $CH_4$ (832) to generate $H_2$-dense fuel 850, such as methanol. Byproducts can be harvested and repurposed or recycled in a reaction with hydrogen produced from biomass dissociation to continuously repeat the cycle, or used as feedstock into other processes, such as the production of carbon-based durable goods.

The generated $H_2$-dense fuel mixture 850 can be storable and transportable. Because the $H_2$-dense fuel mixture 850 can carry $H_2$ fuel in a transportable form, the $H_2$-dense fuel mixture can operate as a vehicle for carrying energy to a desired destination. The $H_2$-dense fuel 850 mixture can be dissociated to obtain $H_2$ fuel and oxygenated fuel using a renewable fuel generation system 860.

In some implementations, to obtain the $H_2$-dense fuel mixture 850, system 800 can include a reaction zone 840 to receive one or more catalysts that enhances the generation of the $H_2$-dense fuel mixture. Examples of catalysts have been described above. In other implementations, a reaction zone 840 can enhance the generation of the $H_2$-dense fuel mixture through the addition of pressure and/or heat.

Figure 8B:
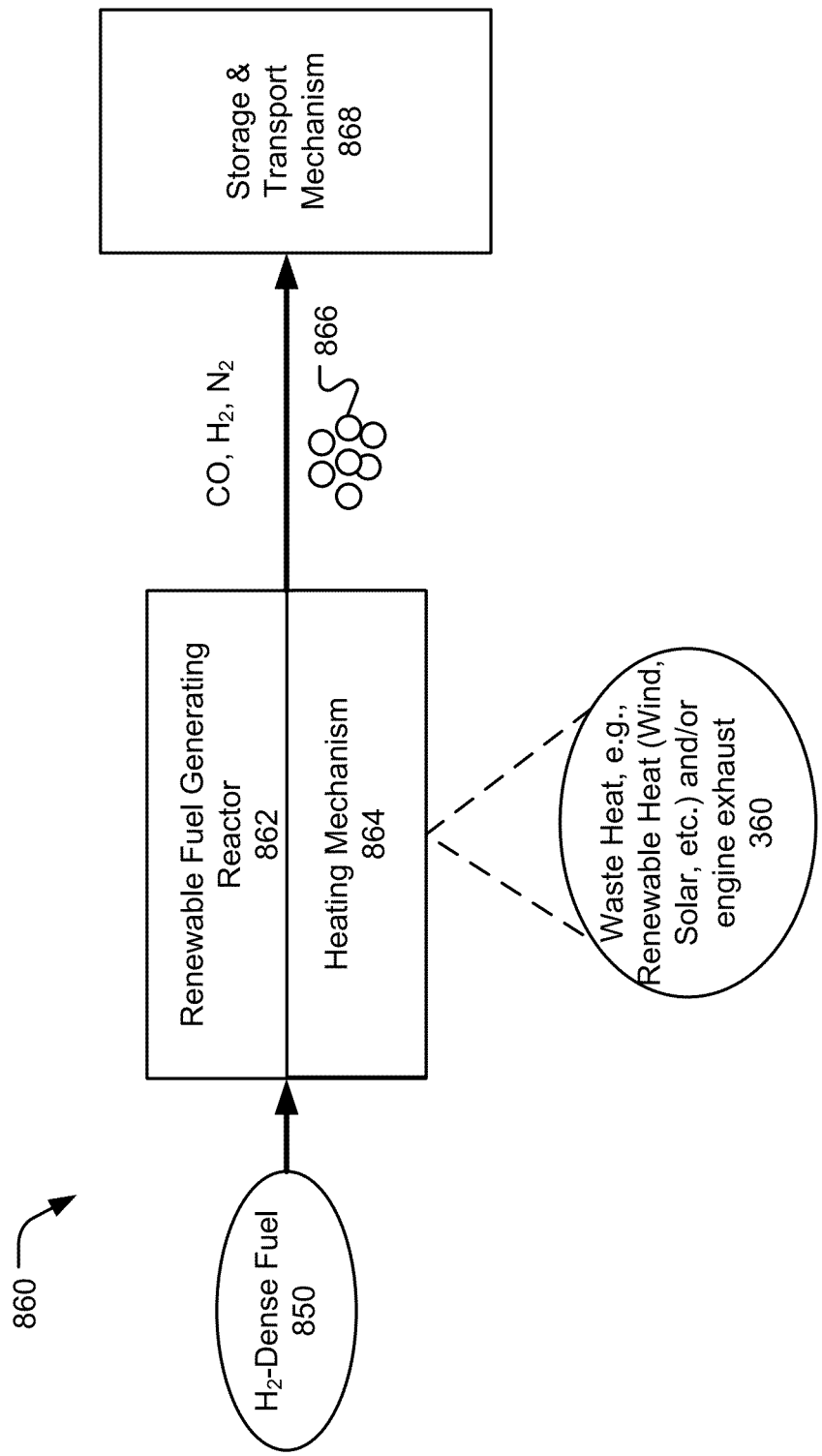
FIG. 8B shows a block diagram of an exemplary system for generating multi-purpose $H_2$-dense fuel mixtures and isolating products and storing energy.

FIG. 8B shows a block diagram of an exemplary system 860 for generating multi-purpose $H_2$-dense fuel mixtures and isolating hazardous and/or useful products and storing energy, as described above. The system 860 can include a renewable fuel generating reactor 862 that receives the $H_2$-dense fuel 850 generated as described above. The renewable fuel generating reactor 862 can include a heating mechanism 864 to apply heat necessary to covert the $H_2$-dense fuel mixture into renewable fuel and nutrients 866, such as carbon, carbon oxides, hydrogen, and nitrogen. The heat used in the reaction can be obtained from waste heat 360, 361 from engine exhaust or cooling system that otherwise would be released to the environment. Also, heat from one or more renewable resources, such as wind, solar, running water, geothermal, etc. can be used in the reaction. The dissociated byproducts from the renewable fuel generating reactor 862 can be subsequently generated into carbon-based durable goods, as described in the U.S. patent application Ser. No. 13/027,068, now issued as U.S. Pat. No. 8,318,997, entitled "CARBON-BASED DURABLE GOODS AND RENEWABLE FUEL FROM BIOMASS WASTE DISSOCIATION," the entire contents of which is incorporated by reference. The generated renewable fuel and nutrients 866 can be stored and/or transported to other location using storage and transport mechanism 868, such as a pressurized container or pipelines.

Tangible and Useful Applications

The ethanol industry has developed an excellent market opportunity for methanol production. Ethanol plants emit millions of tons of $CO_2$ each year through the fermentation process. This $CO_2$ can be readily collected and combined with hydrogen to produce methanol. A 50 million gallon per year ethanol plant would produce an additional 30 million gallons of methanol from the waste $CO_2$ emissions. This would improve the productivity of the ethanol plant by 60% along with the ability to convert much less expensive feedstocks such as stover, straw, and other crop wastes along with energy crops such as elephant grass, various wood wastes including pre-emptive removal of forest fire hazards, switch grass, and noxious weed removal.

One of the key factors to producing alcohols such as methanol along with ethanol from this process at a competitive price is the concentrated supply of carbon dioxide from fermentation processes. Most ethanol plants already have the transportation and un-loading arrangements for bulk deliveries of feed stocks and loading systems to rail or trucks for bulk sales of alcohols along with the basic production infrastructure for increased volumes of liquid transportation fuels.

In some implementations, methanol can be used to "denature" ethanol, replacing costly gasoline.

Applying the described techniques to new ethanol plants currently under construction can potentially provide an additional 5 billion gallons of environmentally friendly alternative liquid fuels annually through far better use of the waste $CO_2$ emissions from the fermentation process of conventional ethanol plants. The resulting environmental impact would be the same as using hydrogen in fuel cells and converted engines that utilize such fuels.

In some implementations, the contaminated or 'dirty' carbon dioxide harvested from various industrial processes as described above can be cleaned and used as nutrients (e.g., along with water) for greenhouse crops. In addition, the clean carbon dioxide can be used as a buoyant lifter or pump in photosynthesis for plants, such as algae. Thus, the cleaned carbon dioxide can be recycled and repurposed as plant nutrients or a pump in photosynthetic reactions.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Only a few implementations and examples are described and other implementations, enhancements and variations can be made based on what is described and illustrated in this application. For example, the described techniques, systems and apparatus can be implemented to provide carbon extraction from any hydrogen and carbon containing material. The extracted carbon can be used to manufacture equipment to harness solar, wind, moving water, and geothermal resources along with transportation components that are stronger than steel and lighter than aluminum. Also, application of such extracted carbon to produce these equipments can provide many times more clean energy than burning the carbon one time and incurring resulting environmental pollution and greenhouse gas problems.

To the extent not previously incorporated herein by reference, the present application incorporates by reference in their entirety the subject matter of each of the following materials: U.S. patent application Ser. No. 12/857,553, filed on Aug. 16, 2010, now issued as U.S. Pat. No. 8,940,265, and titled "SUSTAINABLE ECONOMIC DEVELOPMENT THROUGH INTEGRATED PRODUCTION OF RENEWABLE ENERGY, MATERIALS RESOURCES, AND NUTRIENT REGIMES"; U.S. patent application Ser. No. 12/857,541, filed on Aug. 16, 2010 and titled "SYSTEMS AND METHODS FOR SUSTAINABLE ECONOMIC DEVELOPMENT THROUGH INTEGRATED FULL SPECTRUM PRODUCTION OF RENEWABLE ENERGY"; U.S. patent application Ser. No. 12/857,554, filed on Aug. 16, 2010, now issued as U.S. Pat. No. 8,808,529, and titled "SYSTEMS AND METHODS FOR SUSTAINABLE ECONOMIC DEVELOPMENT THROUGH INTEGRATED FULL SPECTRUM PRODUCTION OF RENEWABLE MATERIAL RESOURCES USING SOLAR THERMAL"; U.S. patent application Ser. No. 12/857,502, filed on Aug. 16, 2010, now issued as U.S. Pat. No. 9,097,152, and titled "ENERGY SYSTEM FOR DWELLING SUPPORT"; U.S. patent application Ser. No. 13/027,235, filed on Feb. 14, 2011, now issued as U.S. Pat. No. 8,313,556, and titled "DELIVERY SYSTEMS WITH IN-LINE SELECTIVE EXTRACTION DEVICES AND ASSOCIATED METHODS OF OPERATION"; U.S. Patent Application No. 61/401,699, filed on Aug. 16, 2010 and titled "COMPREHENSIVE COST MODELING OF AUTOGENOUS SYSTEMS AND PROCESSES FOR THE PRODUCTION OF ENERGY, MATERIAL RESOURCES AND NUTRIENT REGIMES"; U.S. patent application Ser. No. 13/027,208, filed on Feb. 14, 2011, now issued as U.S. Pat. No. 8,318,131, and titled "CHEMICAL PROCESSES AND REACTORS FOR EFFICIENTLY PRODUCING HYDROGEN FUELS AND STRUCTURAL MATERIALS, AND ASSOCIATED SYSTEMS AND METHODS"; U.S. patent application Ser. No. 13/026,996, filed on Feb. 14, 2011 and titled "REACTOR VESSELS WITH TRANSMISSIVE SURFACES FOR PRODUCING HYDROGEN-BASED FUELS AND STRUCTURAL ELEMENTS, AND ASSOCIATED SYSTEMS AND METHODS"; U.S. patent application Ser. No. 13/027,015, filed on Feb. 14, 2011 and titled "CHEMICAL REACTORS WITH RE-RADIATING SURFACES AND ASSOCIATED SYSTEMS AND METHODS"; U.S. patent application Ser. No. 13/027,244, filed on Feb. 14, 2011 and titled "THERMAL TRANSFER DEVICE AND ASSOCIATED SYSTEMS AND METHODS,"; U.S. patent application Ser. No. 13/026,990, filed on Feb. 14, 2011, now issued as U.S. Pat. No. 8,187,549, and titled "CHEMICAL REACTORS WITH ANNULARLY POSITIONED DELIVERY AND REMOVAL DEVICES, AND ASSOCIATED SYSTEMS AND METHODS"; U.S. patent application Ser. No. 13/027,181, filed on Feb. 14, 2011, now issued as U.S. Pat. No. 8,187,550, and titled "REACTORS FOR CONDUCTING THERMOCHEMICAL PROCESSES WITH SOLAR HEAT INPUT, AND ASSOCIATED SYSTEMS AND METHODS"; U.S. patent application Ser. No. 13/027,215, filed on Feb. 14, 2011, now issued as U.S. Pat. No. 8,318,269, and titled "INDUCTION FOR THERMOCHEMICAL PROCESS, AND ASSOCIATED SYSTEMS AND METHODS"; U.S. patent application Ser. No. 13/027,198, filed on Feb. 14, 2011 and titled "COUPLED THERMOCHEMICAL REACTORS AND ENGINES, AND ASSOCIATED SYSTEMS AND METHODS"; U.S. Patent Application No. 61/385,508, filed on Sep. 22, 2010 and titled "REDUCING AND HARVESTING DRAG ENERGY ON MOBILE ENGINES USING THERMAL CHEMICAL REGENERATION"; U.S. patent application Ser. No. 13/027,060, filed on Feb. 14, 2011, now issued as U.S. Pat. No. 8,318,100, and titled "REACTOR VESSELS WITH PRESSURE AND HEAT TRANSFER FEATURES FOR PRODUCING HYDROGEN-BASED FUELS AND STRUCTURAL ELEMENTS, AND ASSOCIATED SYSTEMS AND METHODS"; U.S. Patent Application No. 61/237,419, filed on Aug. 27, 2009 and titled "CARBON SEQUESTRATION"; U.S. patent application Ser. No. 13/027,068, filed on Feb. 14, 2011, now issued as U.S. Pat. No. 8,318,997, and titled "SYSTEM FOR PROCESSING BIOMASS INTO HYDROCARBONS, ALCOHOL VAPORS, HYDROGEN, CARBON, ETC."; U.S. patent application Ser. No. 13/027,195, filed on Feb. 14, 2011, now issued as U.S. Pat. No. 8,784,095, and titled "OXYGENATED FUEL"; U.S. Patent Application No. 61/237,425, filed on Aug. 27, 2009 and titled "OXYGENATED FUEL PRODUCTION"; U.S. patent application Ser. No. 13/027,197, filed on Feb. 14, 2011, now issued as U.S. Pat. No. 8,070,835, and titled "MULTI-PURPOSE RENEWABLE FUEL FOR ISOLATING CONTAMINANTS AND STORING ENERGY"; U.S. Patent Application No. 61/421,189, filed on Dec. 8, 2010 and titled "LIQUID FUELS FROM HYDROGEN, OXIDES OF CARBON, AND/OR NITROGEN; AND PRODUCTION OF CARBON FOR MANUFACTURING DURABLE GOODS"; and U.S. patent application Ser. No. 13/027,185, filed on Feb. 14, 2011, now issued as U.S. Pat. No. 8,328,888, and titled "ENGINEERED FUEL STORAGE, RESPECIATION AND TRANSPORT".

I claim:

1. A method for producing a liquid fuel substance, comprising:
    extracting carbon dioxide from the atmosphere;
    obtaining a first amount of hydrogen as a by-product from a production process to produce a carbon-based article including the dissociation of a waste;
    reacting the carbon dioxide with the first amount of hydrogen to produce a liquid fuel, wherein the produced liquid fuel includes a greater density of hydrogen than that of the waste; and
    dissociating the produced liquid fuel by adding energy to produce fuel constituents including oxides of carbon, and a second amount of hydrogen.

2. The method of claim 1, wherein the first amount of hydrogen is produced by reformation or dissociation of a substance that contains hydrogen.

3. The method of claim 1, further comprising:
    using the liquid fuel in a combustion engine without causing a net gain in the concentration of carbon dioxide in the atmosphere.

4. The method of claim 1, wherein the first amount of hydrogen is coproduced with carbon that is utilized in non-fuel applications.

5. The method of claim 1, wherein the produced liquid fuel includes improved properties from that of the hydrogen from the waste, the improved properties including one or more of storability, transportability, energy density, and combustion characteristics.

6. The method of claim 1, wherein the production process to produce a carbon-based article includes thermal dissociation of natural gas using heat energy or electrical energy is supplied by one or more of an engine, a solar concentrator, a solar energy generator, a wind generator, a hydro energy generator, or a geothermal energy generator.

7. The method of claim 1, wherein the liquid fuel includes at least one of an alcohol or an ether.

8. The method of claim 1, wherein the extracted carbon dioxide from the atmosphere is extracted from one or more of an ethanol plant, bakery, brewery, waste water digester, or permafrost.

9. The method of claim 1, wherein the added energy includes at least one of heat energy or electrical energy supplied by one or more of an engine, a solar concentrator, a solar energy generator, a wind generator, a hydro energy generator, or a geothermal energy generator.

10. The method of claim 1, further comprising:
    reacting the produced liquid fuel with water to produce an oxide of carbon and hydrogen.

11. The method of claim 10, further comprising:
    adding heat energy in the reacting of the produced liquid fuel and the water to produce the hydrogen and carbon dioxide or carbon monoxide,
    wherein the heat energy is supplied by one or more of an engine, a solar concentrator, a solar energy generator, a wind generator, a hydro energy generator, or a geothermal energy generator.

12. The method of claim 10, wherein the produced oxide of carbon includes carbon dioxide, and the method further comprising:
    repurposing the carbon dioxide back to the reacting process to produce the liquid fuel.

13. The method of claim 1, further comprising:
    during the reacting, adding a catalyst to increase a rate of production of the liquid fuel.

14. The method of claim 1, further comprising:
    applying pressure and heat to affect equilibrium of reaction of the carbon dioxide and the hydrogen to produce the liquid fuel.

* * * * *